US010117594B2

(12) United States Patent
Zeng et al.

(10) Patent No.: US 10,117,594 B2
(45) Date of Patent: Nov. 6, 2018

(54) ANALYSIS AND DETECTION FOR ARRHYTHMIA DRIVERS

(71) Applicant: CARDIOINSIGHT TECHNOLOGIES, INC., Independence, OH (US)

(72) Inventors: Qingguo Zeng, Solon, OH (US); Ping Jia, Solon, OH (US); Ryan Bokan, Cleveland, OH (US); Brian P. George, Cleveland, OH (US); Charulatha Ramanathan, Solon, OH (US); Venkatesh Vasudevan, Pepper Pike, OH (US); Maria Strom, Moreland Hills, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 0 days.

(21) Appl. No.: 15/240,636

(22) Filed: Aug. 18, 2016

(65) Prior Publication Data

US 2016/0354004 A1 Dec. 8, 2016

Related U.S. Application Data

(63) Continuation of application No. 14/273,458, filed on May 8, 2014, now Pat. No. 9,427,169.

(Continued)

(51) Int. Cl.
*A61B 5/0452* (2006.01)
*A61B 18/02* (2006.01)
(Continued)

(52) U.S. Cl.
CPC ............ *A61B 5/0452* (2013.01); *A61B 18/02* (2013.01); *A61B 18/04* (2013.01);
(Continued)

(58) Field of Classification Search
CPC ......... A61B 34/10; A61B 18/02; A61B 18/04; A61B 18/1492; A61B 2034/105;
(Continued)

(56) References Cited

U.S. PATENT DOCUMENTS 9,427,169 B2 * 8/2016 Zeng .................. A61B 5/0452
2010/0094274 A1    4/2010 Narayan et al.
(Continued)

FOREIGN PATENT DOCUMENTS

CN    102245091 A    11/2011
CN    102817638 A    12/2012
(Continued)

OTHER PUBLICATIONS

Rogers et al. "Incidence, Evolution, and Spatial Distribution of Functional Reentry During Ventricular Fibrillation in Pigs." Circulation Research, 84:945-954, American Heart Associate. 999, pp. 945-954.*

(Continued)

*Primary Examiner* — Carl H Layno
*Assistant Examiner* — Erin M Piateski
(74) *Attorney, Agent, or Firm* — Tarolli, Sundheim, Covell & Tummino LLP

(57) ABSTRACT

Systems and methods are provided to detect and analyze arrhythmia drivers. In one example, a system can include a wave front analyzer programmed to compute wave front lines extending over a surface for each of the plurality of time samples based on phase information computed from electrical data at nodes distributed across the surface. A trajectory detector can be programmed to compute wave break points for each of the wave front lines and to determine a trajectory of at least one rotor core across the surface.

(Continued)

A stability detector can be programmed to identify at least one stable rotor portion corresponding to subtrajectories of the determined trajectory.

18 Claims, 18 Drawing Sheets

Related U.S. Application Data

(60) Provisional application No. 61/821,170, filed on May 8, 2013, provisional application No. 61/935,584, filed on Feb. 4, 2014.

(51) Int. Cl.

| | | |
|---|---|---|
| A61B 18/14 | (2006.01) | |
| A61B 34/10 | (2016.01) | |
| A61N 1/05 | (2006.01) | |
| A61N 1/362 | (2006.01) | |
| A61N 7/00 | (2006.01) | |
| G06F 19/00 | (2018.01) | |
| G06F 17/50 | (2006.01) | |
| A61B 18/04 | (2006.01) | |
| G16H 50/50 | (2018.01) | |
| A61B 18/00 | (2006.01) | |

(52) U.S. Cl.
CPC .......... *A61B 18/1492* (2013.01); *A61B 34/10* (2016.02); *A61N 1/056* (2013.01); *A61N 1/3622* (2013.01); *A61N 7/00* (2013.01); *G06F 17/50* (2013.01); *G06F 19/00* (2013.01); *G16H 50/50* (2018.01); *A61B 2018/00839* (2013.01); *A61B 2018/0212* (2013.01); *A61B 2034/105* (2016.02); *A61N 2007/0043* (2013.01)

(58) Field of Classification Search
CPC .. A61B 2018/00839; A61B 2018/0212; A61N 1/056; A61N 1/3622; A61N 7/00; A61N 2007/0043; G06F 17/50; G06F 19/3437
USPC ......................................................... 600/515
See application file for complete search history.

(56) References Cited

U.S. PATENT DOCUMENTS

2011/0251505 A1   10/2011   Narayan et al.
2013/0006131 A1*  1/2013    Narayan ................ A61B 5/042
                                              600/508

FOREIGN PATENT DOCUMENTS

| WO | 2012/037471 A2 | 3/2012 |
|---|---|---|
| WO | 2012037471 | 3/2012 |
| WO | 2012/092016 A1 | 7/2012 |
| WO | 2012092016 | 7/2012 |

OTHER PUBLICATIONS

Tusscher et al. Organization of Ventricular Fibrillation in the Human Heart. Circulation Research, American Heart Association. May 31, 2007, pp. 1-15.*

Rogers et al. "Quantitative Techniques for Analyzing High-Resolution Cardiac-Mapping Data.", IEEE Engineering in medicine and Biology. Jan./Feb. 1998, pp. 62-72.*

S. V. Pandit et al.: "Rotors and the Dynamics of Cardiac Fibrillation", Circulation Research., vol. 112, No. 5., Feb. 28, 2013, pp. 849-862.

European Patent Application No. EP14795164, Supplementary European Search Report, Date of Completion: Nov. 11, 2016, 2 pgs.

International Search Report and Written Opinion; International Application No. PCT/US2014/037391 Filed May 8, 2014; Applicant: CardioInsight Technologies, Inc.; dated Oct. 6, 2014; 16 pgs.

Rogers, et al., Quantitative Techniques for Analyzing High-Resolution Cardiac-Mapping Data; IEEE Engineering in Medicine and Biology. Jan./Feb. 1998 [retrieved Aug. 24, 2014]; Retrieved from the Internet: URL:http://phdtree.org/pdf/1235414-quantitative-techniques-for-analyzing-high-resolution-cardiac-mapping-data/>; pp. 62-72.

Tusscher, et al., "Organization of Ventricular Fibrillation in the Human Heart"; Circulation Research, American Heart Association; May 31, 2007 [retrieved Aug. 27, 2014]; Retrieved from the Internet: URL:http://www-binf.bio.uu.nl/khwituss/Publications/CircRes.pdf; pp. 1-15.

Rogers, et al., Evolution, and Spatial Distribution of Functional Reentry During Ventricular Fibrillation in Pigs. Circulation Research, 84:945-954, American Heart Association. 1999 [retrieved Aug. 28, 2014]. Retrieved from the Internet: URL:http://circres.ahajournals.org/content/84/8/945.full, pp. 945-954.

Chinese Application No. 201480025828.0, Filed: May, 8, 2014; Title: Analysis and Detection for Arhythmia Driver; Chinese Office Action dated Oct. 23, 2017; 11 pgs.

* cited by examiner

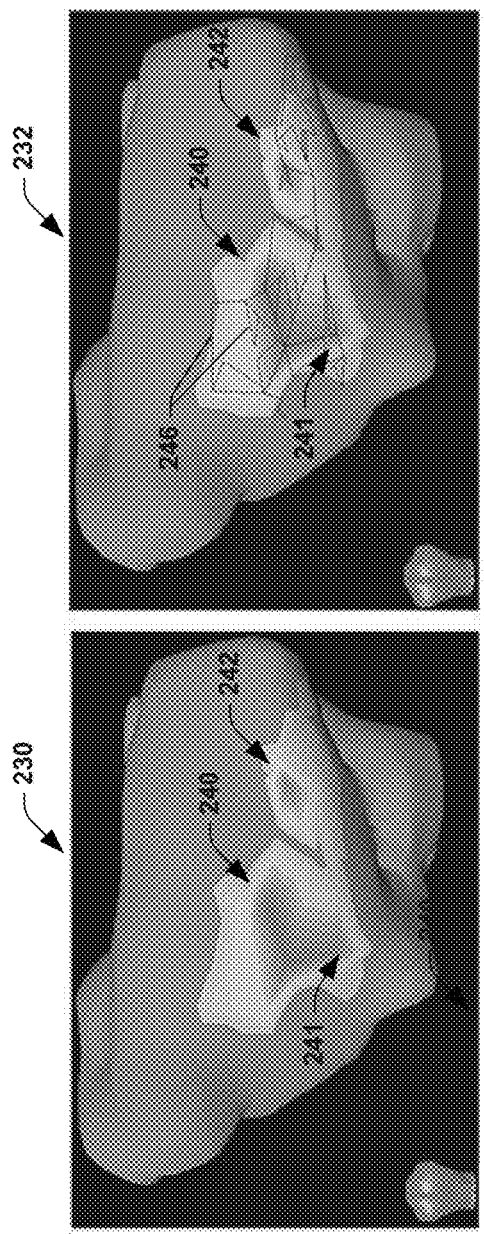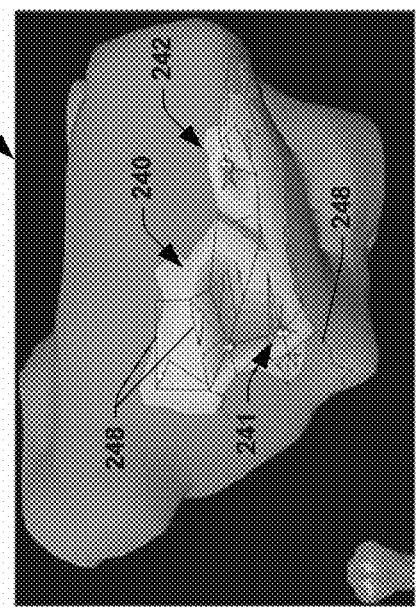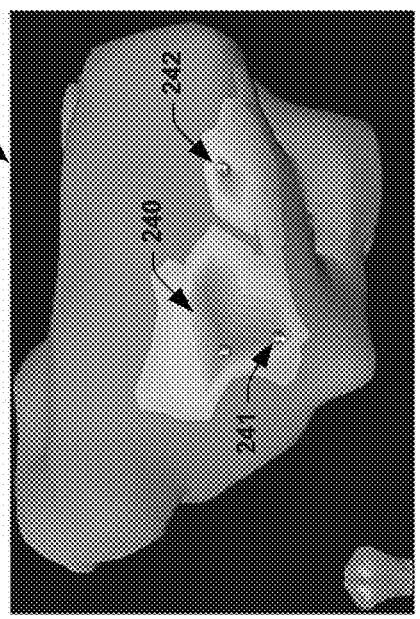

ANALYSIS AND DETECTION FOR ARRHYTHMIA DRIVERS

RELATED APPLICATIONS

This application is a continuation of U.S. application Ser. No. 14/273,458 filed May 8, 2014, now U.S. Pat. No. 9,427,169, issued Aug. 30, 2014, and entitled ANALYSIS AND DETECTION FOR ARRYTHMIA DRIVERS which claims the benefit of U.S. Provisional Patent Application No. 61/821,170, filed May 8, 2013, and entitled SYSTEM AND METHOD TO GENERATE ROTOR CORE TRAJECTORY, and claims the benefit of U.S. Provisional Patent Application No. 61/935,584, filed Feb. 4, 2014, and entitled STABLE ROTOR IDENTIFICATION. The entire contents of each of the above identified applications are incorporated herein by reference.

TECHNICAL FIELD

This disclosure relates to analysis and detection for arrhythmia drivers.

BACKGROUND

Cardiac arrhythmia, also known as dysrhythmia, refers generally to any of a group of conditions in which the electrical activity of the heart is irregular or is faster or slower than normal. Arrhythmias can occur in the upper chambers of the heart, or in the lower chambers of the heart. Arrhythmias may occur at any age. Some are barely perceptible, whereas others can be more dramatic and can even lead to sudden cardiac death.

SUMMARY

This disclosure relates to analysis and detection for arrhythmia drivers.

In one example, a non-transitory computer-readable medium can include instructions executable by a processor, which instructions programmed to perform a method. The method can include determining a pair of wave break points for each identified wave front line at a given time sample of a plurality of time samples. For each other of the plurality of time samples, the method can include:
  evaluating a spatial distance for a given wave break point relative to each active trajectory in a previous time sample to identify a closest active trajectory, each respective trajectory in the previous time sample being an active trajectory if updated within a predetermined time period from a current time sample time; and
  appending the given wave break point to update the closest active trajectory based on the evaluating.
The evaluating and the appending can be repeated for each wave break point over the plurality of time samples to generate a set of one or more rotor trajectories.

Another example can provide a system that includes a wave front analyzer programmed to compute wave front lines extending over a surface for each of the plurality of time samples based on phase information computed from electrical data at nodes distributed across the surface. A trajectory detector can be programmed to compute wave break points for each of the wave front lines and to determine a trajectory of at least one rotor core across the surface. A stability detector can be programmed to identify stable rotor portion(s) corresponding to subtrajectories of the determined trajectory.

As yet another example, a method can include determining a wave front on a geometric surface based on evaluating computed phase values for each of a plurality nodes distributed across the geometric surface for each of a plurality of time samples over at least one time interval. The determined wave front can be stored in memory as wave front data. The method can also include determining a trajectory of a rotor core over the at least one time interval. The determined trajectory can be stored in the memory as trajectory data. The method can also include evaluating an indication of stability for the rotor over the at least one time interval to identify stable portion(s) for the rotor based on analyzing the trajectory data and the wave front data.

In some examples, the systems and methods can store computed information as arrhythmia driver data. The arrhythmia driver data can be employed to generate one or more graphical maps for each such arrhythmia driver. In other examples, the arrhythmia driver data can be used to control a therapy system that is configured to deliver a therapy to a patient.

BRIEF DESCRIPTION OF THE DRAWINGS

FIGS. 9A, 9B, 9C and 9D depict examples of different stable rotor maps that can be generated.

DETAILED DESCRIPTION

This disclosure provides system and methods for analysis and detection of arrhythmia drivers. In one example, one or more wave front lines can be computed across a geometric surface over time and corresponding wave break points can be detected for each of the wave front lines. The wave break points, for example, can correspond to end points along each wave front line at a given time over a corresponding interval. One or more rotor core trajectories can be determined from the wave break points over a given time interval based on analyzing spatial and/or temporal characteristics of the wave break points over the given interval. Each rotor trajectory thus provides a path of travel for a respective rotor core in the direction of the respective wave front lines. As used herein, the terms "rotor", "rotor core" and related rotor information can refer to any re-entrant arrhythmia, including micro and/or micro re-entry, which can be a driver for arrhythmia.

Additionally or alternatively, one or more spatially stable portion of each rotor can also be identified. For example, rotation angles and corresponding rotor statistics can also be computed for each identified stable rotor over time. The rotor statistics can also be utilized to filter the respective rotors by setting thresholds (e.g., user programmable or default thresholds), which can in turn be utilized to identify stable rotors associated with each of the respective trajectories. Further statistics and dynamic characteristics can be computed for each of the identified stable rotors, as well as one or more proximal regions. Various other outputs (e.g., rotor maps) can be generated as well. In some examples, connectivity among different stable rotors can also be determined, such as corresponding to stable portions of rotor core trajectories that are linked by one or more wave front lines over a time period. As another example, an indication of sustainability for one or more drivers of arrhythmia can also be determined. The indication of sustainability can computed as a local (e.g., regional) or global, and a corresponding output can be generated.

While many examples of rotor and stability detection are disclosed with respect to reconstructed electrograms on a cardiac envelope or cardiac surface, the system and method disclosed herein are equally applicable to any electrical signals for a geometric surface, whether measured directly for the surface or derived (e.g., reconstructed) from measurements. Additionally, while many examples herein are described in the context of rotor detection and analysis for cardiac electrical signals, it is to be understood that the approaches disclosed herein are equally applicable to other electrophysiological signals, such as electroencephalography, electromyography, electrooculography and the like. That is, the system and method disclosed herein can be applied on any temporal phase signal that can be acquired from or calculated for a surface.

Figure 1:
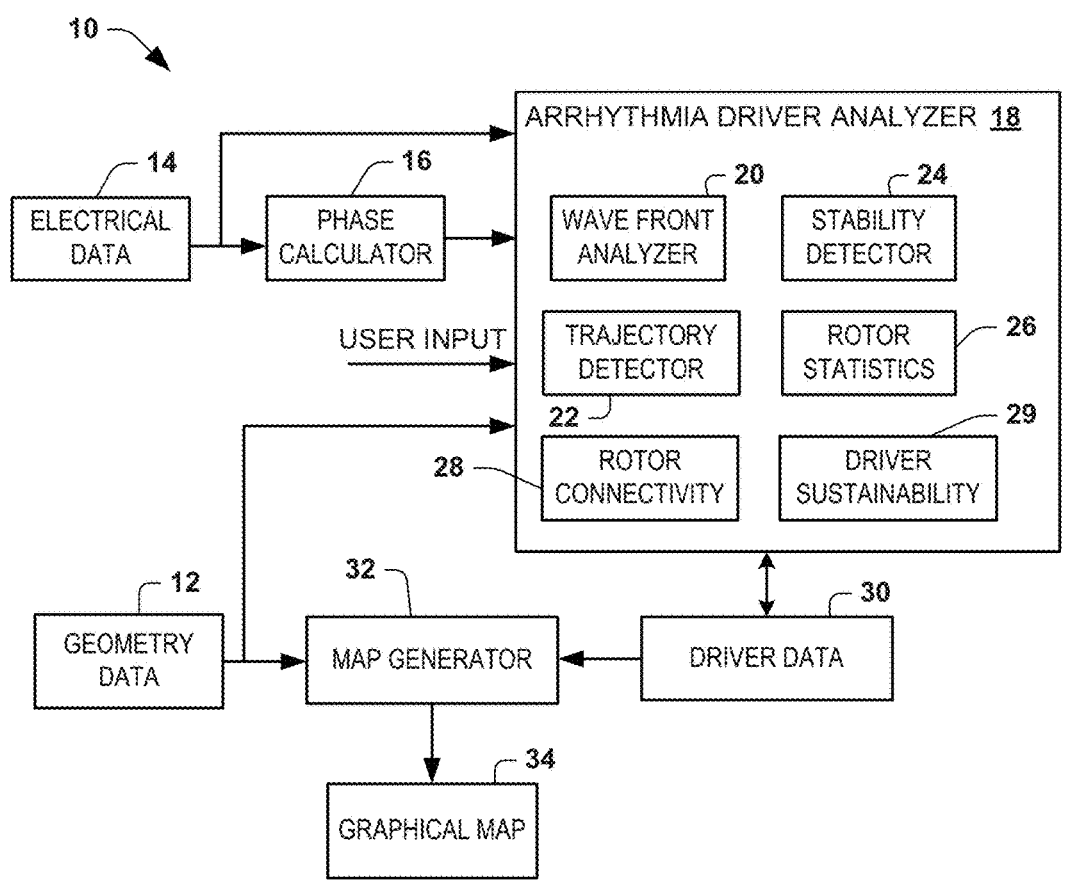
FIG. 1 depicts an example of a system to analyze and detect arrhythmia drivers.

FIG. 1 depicts an example of a system 10 to detect and analyze arrhythmia drivers, such as associated with rotors. As used herein, in the context of cardiac electrophysiology, the term rotor can refer to an organizing source of any electrical activity for the heart. Evidence supports a significant role for rotors as drivers for various types of arrhythmias, such as tachycardia, bradycardia and fibrillation. Thus, the system 10 can analyze geometry data 12 and electrical data 14 (e.g., collectively corresponding to electroanatomic data) to provide rotor data 30 based on which one or more corresponding graphical maps 34 (e.g., electrophysiological map) can be generated. For example, the electrical data 14 can be stored with the geometry data 12 in memory (e.g., one or more non-transitory computer readable media) as electroanatomic data that describes electrical activity at a plurality of anatomical locations (e.g., nodes) for one or more time intervals. For example, the electrical data 14 can be provided as electrograms or other electrical waveforms representing electrical activity for the anatomical locations distributed across a geometric surface.

As disclosed herein, the anatomical locations can be represented as nodes distributed (e.g., an even distribution) over a geometric surface, represented by the geometry data 12. The geometric surface can be a surface of an anatomical structure, such as tissue of a patient (e.g., human or other animal). In some examples, the patient tissue can be cardiac tissue, such that the geometric surface corresponds to an epicardial surface, an endocardial surface or another cardiac envelope. The geometric surface can be patient specific (e.g., based on imaging data for the patient), it can be a generic model of the surface or it can be a hybrid version of a model that is customized based on patient-specific data (e.g., imaging data, patient measurements, reconstructed data, and/or the like). The electrical data 14 thus can characterize electrical potentials for nodes distributed across any such geometric surface, such as tissue of the patient. As disclosed herein, the geometric surface can be defined by geometry data 12 that is stored in memory.

As a further example, the electrical data 14 can correspond to electrophysiological signals, such as can correspond to physiological signals obtained by one or more electrodes or otherwise derived from such signals. For instance, the electrodes can be applied to measure the electrical activity non-invasively, such as may be positioned over a patient's body surface such as the patient's head (e.g., for electroencephalography), a patient's thorax (e.g., for electrocardiography) or other noninvasive locations. The electrical data thus can correspond to the body surface measured electrical signals or, as disclosed herein, be reconstructed onto another surface based on the body surface measurements. In other examples, the input electrical data 14 can be acquired invasively, such as by one or more electrodes positioned within a patient's body (e.g., on a lead or a basket catheter during an EP study or the like). In yet other examples, the input electrical data 14 can include or be derived from a hybrid approach that includes both non-invasively acquired electrical signals and invasively acquired electrical signals.

The electrical data 14 can include electrical activity for nodes on a geometric surface that is defined by the geometry data 12. The geometry data 12 can represent a two-dimensional or a three-dimensional surface for the patient. For example, the geometric surface can be a body surface (e.g., an outer surface of the thorax or portion thereof) where sensors are positioned to measure electrical activity. In other examples, the surface can be a surface of internal tissue or a computed envelope having a prescribed position relative to certain internal tissue. Depending on the geometric surface for which the electrical data 14 has been provided, the geometry data 12 can correspond to actual patient anatomical geometry (e.g., derived from one or more imaging technologies, such as xray, computed tomography, magnetic resonance imaging or the like), a preprogrammed generic model or a hybrid thereof (e.g., a model that is modified based on patient anatomy). That is, the geometric surface should represent the same surface that contains the nodes represented by the electrical data 14.

The system 10 can include a phase calculator 16 programmed to compute phase of electrical activity for nodes distributed across the geometric surface, corresponding to patient tissue, based on the data 14 representing the electrical activity for the geometric surface over time (e.g., one or more intervals of a plurality of sequential samples of electrical activity). In some examples, the geometric surface can be represented as a mesh including a plurality of nodes interconnected by edges to define the mesh. By way of example, the phase calculator 16 can be programmed to convert each cycle of electrical signal into a periodic signal as a function of time. For example, the phase calculator 16 can assign each point in time in between the beginning and end of each cycle a phase value, such as between $[-\pi$ and $\pi]$ in an increasing manner. The phase calculator 16 can compute the phase information for several time intervals at various points in time to make the analysis robust in terms of temporal and spatial consistency. In some examples, such as for where the electrical data corresponds to or is derived from non-invasively acquired electrical signals, the phase calculator 16 can provide corresponding phase data for each location (e.g., about 2000 or more points) on the cardiac envelope for one or more time intervals for which the electrical data has been acquired. Since the electrical signals can be measured and/or derived concurrently for an entire geometric region (e.g., over up to the entire heart surface), the computed phase data and resulting wave front likewise are spatially and temporally consistent across the geometric region of interest.

An example of how the calculator can determine phase based on electrical data 14 for a surface is disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized to determine phase, however.

The computed phase information provided by the phase calculator 16 can be stored in memory (e.g., as phase data) and utilized by an arrhythmia driver analyzer 18 to detect and characterize rotor dynamics temporally and/or spatially for the geometric surface. In the example of FIG. 1, the analyzer 18 can include a wave front analyzer 20, a trajectory detector 22, a stability detector 24, a rotor statistics component 26 and a rotor connectivity function 28. As disclosed herein, for example, the analyzer 18 can identify locations on the geometric surface corresponding to one or more rotor core trajectories based on wave front data. The analyzer 18 can also detect one or more stable rotor cores and derive related information for one or more of the detected stable rotors. For example, the analyzer 18 can compute statistics for stable rotors across the geometric surface over time and/or ascertain connectivity between rotors. Additionally or alternatively, virtual electrograms, corresponding to waveforms at nodes located around an identified stable rotor core (e.g., a neighborhood of nodes around the rotor core) can be generated. The virtual electrograms can include activation time marking, depolarization time marking or other information (e.g., related statistics, cycle length, dominant frequency, etc.) that can be derived from the respective waveforms that are generated at the neighboring nodes around each stable rotor cores. For example, the analyzer can compute statistics on electrograms for the neighboring nodes around stable rotor cores, which statistics can include mean and standard deviation and other statistical measures for cycle length, amplitude, activation times, depolarization times and the like.

As an example, the wave front analyzer 20 can be configured to compute and identify wave front locations and corresponding wave front lines based upon the phase data computed by the phase calculator 16. The wave front analyzer 20 can determine that an activation time or depolarization begins at a time where the phase signal for a given point (e.g., node on a geometric surface) crosses a selected phase value $\Phi_S$, which can define a phase threshold. The phase threshold $\Phi_S$ for determining an activation or depolarization boundary condition can be fixed for a given application or it can be programmable, such as in response to a user input. The wave front analyzer 20 further can determine which pairs of adjacent nodes across the surface have phase values encompassing the selected phase value $\Phi_S$ the selected phase value at a given time index. In this context, the term encompass means that the selected phase value $\Phi_S$ lies at or between the phase values for such pair of nodes. The term adjacent nodes can refer to nodes that are interconnected to each other by an edge of a meshed surface, for example, or be located within a predetermined distance of each other. For the example where the geometric surface is represented as a mesh of nodes interconnected by edges, the wave front analyzer 20 can determine if the selected phase value $\Phi_S$ is between the phase values $\Phi_i$ and $\Phi_j$ for a pair of adjacent nodes i and j connected by a common edge of the mesh (e.g., $\Phi_i \leq \Phi_S \leq \Phi_j$ or $\Phi_i \geq \Phi_S \geq \Phi_j$). This determination can be repeated for each interconnected node pair across the geometric surface of interest to identify node pairs that encompass the wave front for one or more time intervals.

The wave front analyzer 20 further can determine a location for the wave front across the geometric surface for each time sample index. For example, the wave front location at a given time resides on a path extending between each of the node pairs identified as encompassing the selected phase value $\Phi_S$. For each time index (e.g., sample time), the wave front analyzer 20 can identify a plurality of points that estimate an activation or depolarization time across a geometric surface. These points collectively can define a wave front across the surface for each of a plurality of time indices, and the wave front analyzer 20 can connect such points to provide a corresponding wave front line for a given time index. For example, the wave front analyzer 18 further can be programmed to connect each of the plurality of estimated wave front points by marching through each of the edges of the mesh determined to contain the selected phase value $\Phi_S$. The points through each edge can thus correspond to an intersection point of each edge, and the intersection points can be connected together to represent a corresponding wave front at a given time index. The wave front analyzer 20 can provide wave front data that can specify the points corresponding to wave front locations and corresponding wave front lines.

As one example, the wave front analyzer 20 can be implemented to determine wave front locations and wave front lines as disclosed in International application no. PCT/US14/12051, filed on Jan. 17, 2014, and entitled WAVE FRONT DETECTION FOR ELECTROPHYSI-OLOGICAL SIGNALS, which is incorporated herein by reference. Other methods can also be utilized to determine wave front locations and wave front lines.

The trajectory detector 22 can be configured to determine one or more rotor core trajectories based upon wave front data provided by the wave front analyzer 20. As an example, the trajectory detector 22 can be programmed to detect wave break points for each time sample over one or more time intervals, which can be contiguous or non-contiguous intervals. For example, the wave break points can correspond to end points of each wave front line that has been computed. For the first time sample, each wave break point will initialize a new trajectory and each such trajectory will be active. Then for the remaining time samples in the interval, the trajectory detector 22 can determine wave break points from the end points of a corresponding wave front lines for the next time sample, and so on for each time same. The trajectory detector 22 can be programmed to evaluate each wave break point temporally and spatially to determine whether the wave break point should be added to a respective active rotor core trajectory or if such break point should begin another new trajectory. An active trajectory may become inactive, for example, if there is no wave break points append to it for a certain period (e.g., a predetermined or user-programmable duration threshold, such as about 5 ms). After constructing each trajectory, the trajectory detector can apply a temporal constraint (e.g., a predetermined or user-programmable duration threshold, such as about 100 ms) such that only trajectories that are longer than a prescribed amount of time can be utilized and stored as rotor core trajectory data.

The stability detector 24 can be programmed to identify one or more stable portions of each rotor core trajectory from the rotor core trajectory data. As one example, the stability detector 24 can compute a time-weighted average on the nodes along each trajectory and remove nodes that are further than a predetermined distance from a center (e.g., centroid) of the identified rotor core trajectory. After nodes that are further than the predetermined distance are removed, another average can be computed until all of the remaining points are within a predetermined distance (e.g., a radius) from the center. The process can further be repeated until all of the remaining portions that are not within a predetermined distance of the center have been removed, until they are part of some sub trajectory. As another example, the stability detector 24 can implement a clustering algorithm to cluster wave break points, spatially and temporally, in a given rotor core trajectory based on the predetermined distance for clustering the rotor to determine the stable portions. Each stable rotor portion can define a respective sub-trajectory.

The rotor statistics component 26 can be programmed to compute one or more statistics characterizing static and/or dynamic properties of each stable rotor identified by the stability detector 24. Examples of statistics that the rotor statistics component 26 can compute for each stable rotor include a number of rotations, standard deviations of the number rotations across rotors in a spatial region or the whole surface, an average number of rotations within a predetermined sized spatial region (e.g., a regional average number of rotations), an angular velocity for each rotor, angular accelerations for each rotor and the like.

The rotor connectivity component 28 can determine if a given pair of rotors is connected. By connectivity between a pair of rotors, it is a meant that there are one or more wave front lines linking the pair of identified trajectories. For example, the connectivity component 28 can ascertain that a pair of stable rotors is connected if the rotor core trajectories for such stable rotors are linked over a predetermined period of time or some percentage of time that each rotor is active. The connectivity can be specified for a given trajectory, such as by specifying each wave front line from which a corresponding wave break point in the given trajectory is generated. If two stable rotor trajectories specify the same wave front line over a number of time samples, which can be a predetermined minimum threshold, connectivity between such stable rotors can be ascertained and the rotors can be identified as a stable pairing.

The analyzer 18 can also include a sustainability calculator 29 programmed to compute an indication for sustainability of one or more arrhythmia drivers. For example, the sustainability calculator 29 can compute an indication of rotor sustainability. Additionally or alternatively, the sustainability calculator 29 can compute an indication of sustainability for one or more other arrhythmia drivers. As an example, can the sustainability calculator 29 can determine rotor sustainability corresponding to a number of times each rotor within a defined spatial region continuously rotates, on average, for a given detection. Therefore, each detected rotor in the spatial region will have an associated rotation count, which can be an integer or fractional quantity. The average rotation count of all detections in the entire heart (or other organ) can provide a global rotor sustainability index. The average rotation count of all detections in a given anatomical region of interest can provide a corresponding local rotor sustainability index for each such region. As one example, the sustainability calculator 29 can be programmed to compute a rotor sustainability index for a region (or globally) over a defined time interval (e.g., a duration selected automatically or in response to a user input) as follows:

$$\text{Rotor Sustainability} = \frac{\Sigma \text{ rotor rotations}}{\Sigma \text{ rotor detections}} \qquad \text{Eq. 1}$$

A local region can correspond to a surface region of interest according to anatomical significance and/or based on identifying two or more rotors within a given distance of each other. Additionally or alternatively, the region can be determined automatically or in response to a user input selecting a region of interest with a user interface. While the example of the sustainability calculator 29 is described above in relation to rotor sustainability, sustainability of one or more other arrhythmia drivers (e.g., focal discharge) could also be characterized, and a total sustainability could be computed by aggregating normalized values of the indices computed for each such driver.

The analyzer 18 thus can generate driver data 30, which as mentioned above can include wave front data, rotor core trajectory data, stable rotor data, rotor statistics data, driver sustainability data as well as connectivity data for paired drivers (e.g., rotors and/or foci). A map generator 32 can generate one or more graphical maps 34 based on the driver data 30. In some examples, the geometry for the surface of interest can be part of the rotor data. In other examples, the map generator 32 can employ the rotor data, in conjunction with the geometry data 12, to generate each graphical map 34. The map generator 32 further can be responsive to a user input to control thresholds or other criteria that are utilized as part of the analyzer 18. The resulting graphical map 34 thus can be provided to a display, printed or transferred into another user-perceptible format.

As a further example, the map generator 32 can generate the graphical map 34 to graphically depict one or more locations on the geometric surface corresponding to quantify one or more arrhythmia drivers, as represented by the driver data 30. As mentioned the driver data 30 can include information describing dynamic properties of arrhythmia drivers for a geometric surface of interest front over a plurality of time indices within one or more time intervals. Thus, the map generator 34 can create a graphical map for each of the time indices. For example, presentation of the graphical maps in a sequence in an order of the time indices can demonstrate dynamic behavior of the rotors and other arrhythmia drivers across the geometric surface. While in the example of FIG. 1 the analyzer 18 is demonstrated as being separate from the map generator 32, in other examples, the analyzer methods could be implemented as a module (e.g., machine readable instructions) that is part of the map generator.

The map generator 32 further can be configured to rotate the surface geometry (e.g., a 3-D surface) in response to a user input, such as to reveal other portions of the surface and their wave front activity according to the phase signals that have been computed at such locations, as disclosed herein. Additionally, the graphical map can employ a color coding range or other scale utilized to graphically differentiate the derived driver data 30 being mapped onto the geometric surface. As yet a further example, the systems and methods to perform detection of one or more arrhythmia drivers and related rendering in electrocardiographic maps, as disclosed herein, can be combined with other diagnostic and monitoring tools, which may include therapy delivery, to provide an integrated system (see, e.g., FIG. 4).

Figure 2:
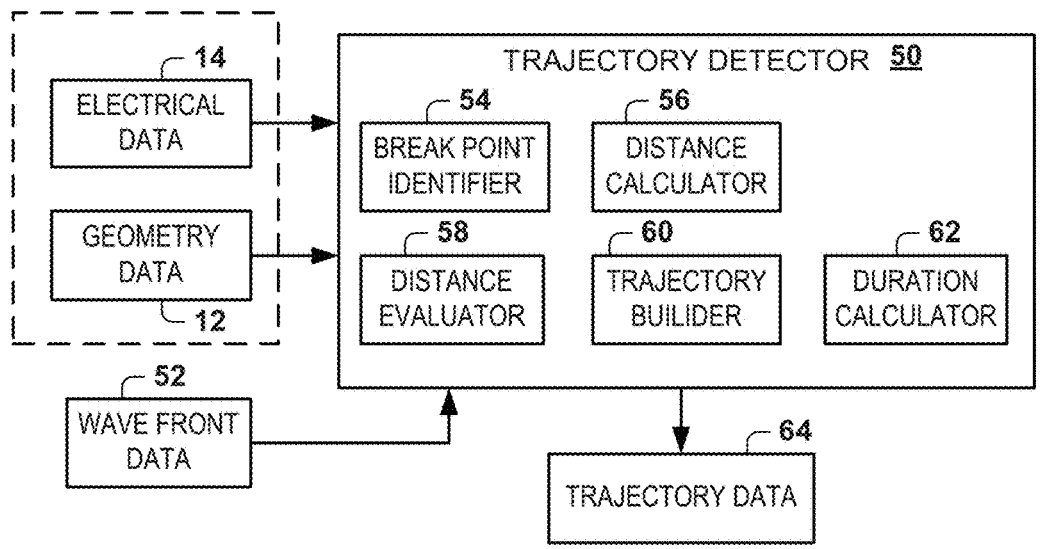
FIG. 2 depicts an example of a trajectory detector that can be implemented.

FIG. 2 depicts an example of a trajectory detector 50 that can be programmed to determine one or more rotor core trajectories across a surface geometry. The trajectory detector 50 can be implemented as the trajectory detector 22 of FIG. 1. For instance, the trajectory detector 50 can be programmed to detect trajectories based on electroanatomic data 51, which can include electrical data 14 and geometry data 12, and wave front data 52 (e.g., computed by wave front analyzer 20 of FIG. 1). In the example of FIG. 2, the trajectory detector 50 can include executable code blocks demonstrated as a break point identifier 54, a distance calculator 56, a distance evaluator 58, a trajectory builder 60 and a duration calculator 62.

By way of example, the break point identifier 54 is programmed to identify break points from wave front lines determined on the geometric surface for each time sample. For instance, the break point identifier 54 can identify end points for each wave front line generated for a given time frame that does not form a loop (e.g., it defines a segment with spaced apart ends). For the first time sample in a given interval (including multiple time samples), the trajectory detector can set each wave break point to initialize a new trajectory and each such trajectory will be active (at least initially). Then for the remaining time samples in the interval, wave break points can be determined in a similar manner, namely from the end points of a corresponding wave front lines for each subsequent time sample.

The distance calculator 56 can be programmed to compute a distance (at least spatially) to determine whether the wave break point should be added to a respective rotor core trajectory. For example, the distance calculator 56 can compute the distance for each wave break point in a current time sample to a last location of all active trajectories from one or more previous time samples. The distance can be entirely spatial, such as a Euclidean distance computed in two or three-dimensional coordinate space of the surface geometry, and/or geodesic distance defined along the surface. In other examples, the distance can also account for the temporal distance. The distance evaluator 58 can be programmed to and identify the closest active trajectory based on the distance values computed by the distance calculator 56.

The trajectory builder 60 can be programmed to construct trajectories from the wave break points identified in the current time sample by appending (or not appending) each such break points to an active trajectory. For instance, the trajectory builder 60 can determine whether the closest active trajectory (determined by the distance evaluator 58) has been updated yet for the current time sample. If the closest active trajectory to a given break point has not yet been updated, the trajectory builder 60 can determine if the distance to such closest active trajectory is less than a predetermined threshold (e.g., about 1 cm to about 2 cm). If it is closer than such threshold, the trajectory builder 60 can append the wave break point to the closest trajectory identified (e.g., that is within the distance threshold and has not yet been updated). If the trajectory builder determines that the closest it is not within the threshold, the trajectory detector can begin a new trajectory with this wave break point. If the closest active trajectory has already been updated, the trajectory builder 60 can branch out to begin a new trajectory from the given wave break point.

The trajectory detector 50 thus can repeat the foregoing process by executing the distance calculator 56, distance evaluator 58 and trajectory builder 60 through the all of the break points in the current time sample. Additionally, the trajectory detector 50 can control the state (e.g., active or inactive) of each trajectory during the process. For example, if after going through such wave break points any trajectory that was active in a previous time frame is not updated by this process for the current time frame (or is not updated across a prescribed number of consecutive time samples), the trajectory detector 50 can change the state of such trajectory an active to an inactive state. The duration calculator 62 can be programmed to perform temporal thresholding by applying a duration threshold to each identified trajectory for a time interval (e.g., multiple time frames). The duration calculator 62 thus can ensure that only trajectories that are longer than the prescribed time threshold can be utilized and stored in memory as trajectory data 64. In this way, the trajectory data 64 can define a subset of rotor trajectories, specifying linked wave break points from different time samples, determined to be active for at least a minimum duration.

Figure 3:
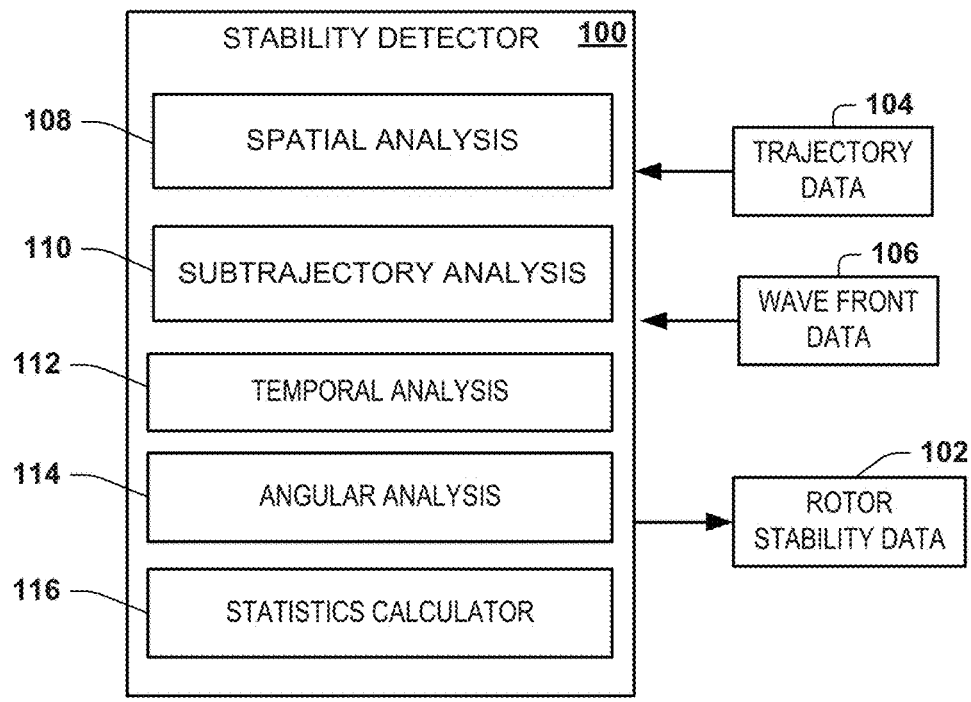
FIG. 3 depicts an example of a stability detector.

FIG. 3 depicts an example of a stability detector 100 that can be programmed to generate rotor stability data 102, based on trajectory data 104 (e.g., computed by trajectory detector 50 of FIG. 2) and wave front data 106 (e.g., computed by wave front analyzer 20 of FIG. 1). The stability detector 100 can be implemented as the stability detector 24 of FIG. 1. The rotor stability data 102 can be utilized to generate one or more graphical maps and/or other outputs, such as disclosed herein. In the example of FIG. 3, the stability detector 100 can include executable code blocks demonstrated as a spatial analysis block 108, a temporal analysis block 110, a subtrajectory analysis block 112, an angular analysis block 114 and statistics calculator 116.

As one example, the spatial analysis block 108 can be programmed to determine spatial stability properties for localized portions of a given trajectory. For example, the spatial analysis block 108 can compute a center for a given trajectory (e.g., a centroid of the trajectory) and apply temporal weighting to compute a time-weighted average for the location of nodes along each trajectory. The temporal weighting can be a linear or non-linear weighting applied to nodes in the given trajectory for determining the centroid. The spatial analysis block 108 can be programmed to compute a distance as a function of the time-weighted location for each node and the computed center. The spatial analysis block 108 can be configured to apply distance criteria and remove each node that is further than a predetermined distance from the center. After one or more nodes that are further than the predetermined distance are removed, the spatial analysis block 108 can compute another time-weighted center until all of the remaining points are within a predetermined distance (e.g., a predetermined radius) from the center to define a corresponding spatial region around the center. The spatial analysis block 108 thus can determine a distance parameter representing at spatial distance for each respective portion of the given trajectory.

The subtrajectory analysis block 110 can a function programmed to analyze continuity among the remaining nodes and group the nodes into one or more subtrajectories. For instance, subtrajectory analysis 110 can compute a duration parameter for nodes in each respective subtrajectory, and evaluate whether nodes in a given subtrajectory has a duration that exceeds a time threshold sufficient to indicate temporal stability. If the subtrajectory does not meet the time threshold, it can be discarded. Each subtrajectory further can be analyzed by the spatial analysis function 108 as mentioned above to confirm sufficient spatial stability.

The temporal analysis block 112 can be programmed to evaluate temporal stability for each corresponding spatial region defined as a subtrajectory with respect to a given centroid. The temporal analysis block 112, for example, can evaluate a time difference between a last time when the subtrajectory exits the spatial region and the first time such subtrajectory enters the spatial region. If this difference is sufficient (e.g., exceeds a threshold), the subtrajectory can be identified as being a stable rotor. As another example, the temporal analysis block 112 can evaluate the time difference between the exit and the next entering. If such difference is very small (e.g., less that a maximum time difference threshold), the portion outside the spatial region can be considered as inside the region. Otherwise, this trajectory can be further split into two subtrajectories. These temporal criteria can be combined together for subsequent analysis and mapping. The data 102 for each node in subtrajectory thus can be identified as part of a particular stable rotor. If the difference does not exceed the threshold, however, it can be disregarded as not being stable.

The angular analysis block 114 can be programmed to compute angular characteristics for each stable rotor portion (e.g., rotor subtrajectories) that is identified. For example, the angular analysis block 114 can compute one or more of a direction of rotation for a given rotor over a plurality of time samples, an angular velocity (direction and rate), rotation rate, angular acceleration as well as direction of rotation. The computed angular information can be stored as part of the rotor stability data that is associated with each node in the identified subtrajectories.

The statistics calculator 116 can be programmed to compute statistics to characterize each identified stable rotor. For example, the statistics calculator 116 can compute one or more statistical parameters for each identified stable rotor, including statistics related to the data generated by the angular analysis block 114 (e.g., direction of rotation, number of rotation data, rotation rate, angular velocity, angular acceleration and the like). The statistics parameters can include a mean, average and/or standard deviation for one or more of the parameters determined by the angular analysis block over an interval including a plurality of time samples. Each of the computed angular statistics parameters, spatial parameters and temporal parameters computed can be stored in memory as part of the rotor stability data.

The stability detector 100 can further programmed with one or more thresholds to filter the identified rotors based on one or any combination of the computed data (e.g., angular statistics, spatial parameters and temporal parameters) to identify whether a given identified rotor is stable. For example, the thresholds can be set to default values or be programmable in response to user inputs to selective configure the filtering applied to the computed rotor data. In this way, a user can refine stability criteria (e.g., corresponding to filter thresholds) that are utilized to identify and locate one or more arrhythmia drivers.

Figure 4:
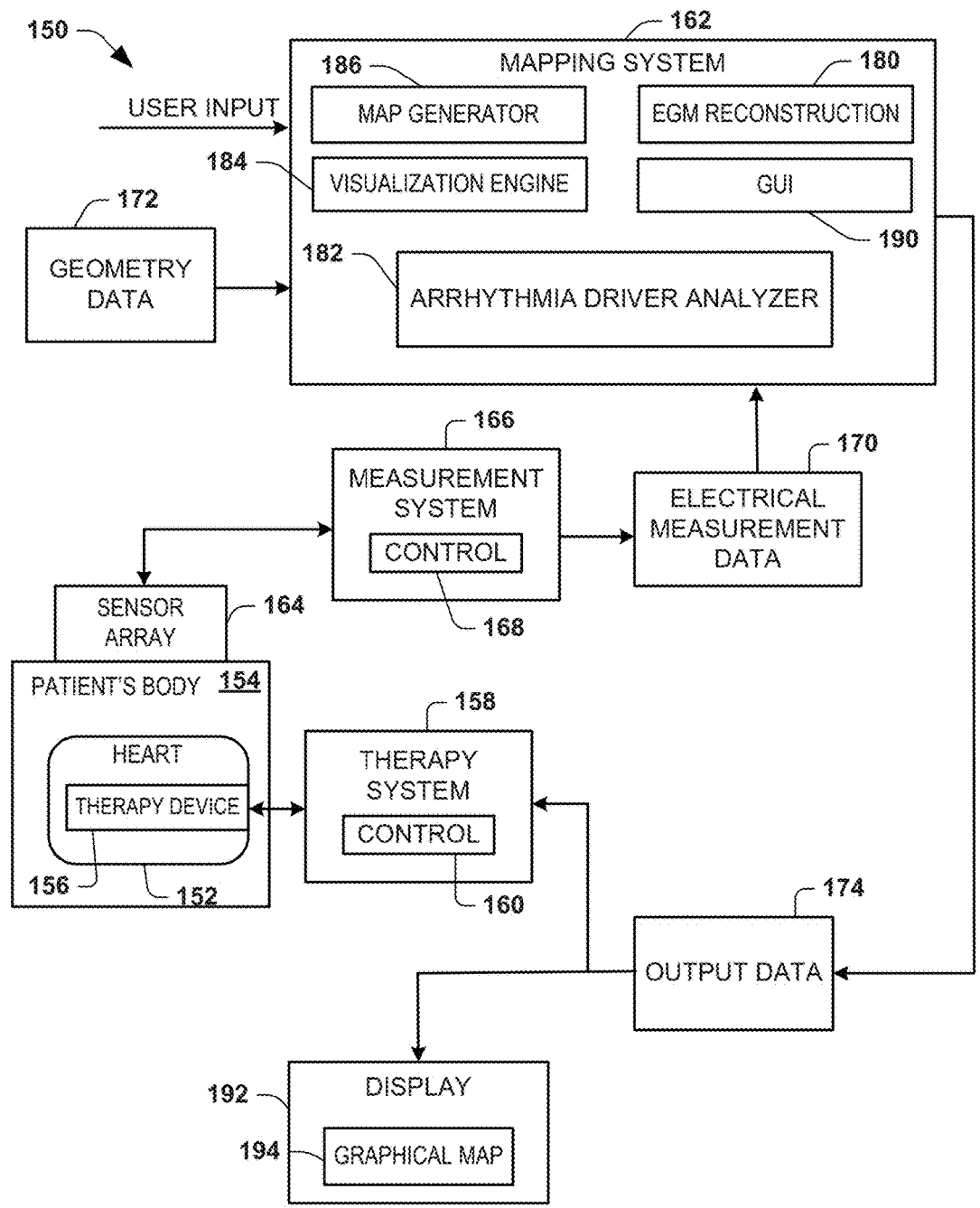
FIG. 4 depicts an example of a mapping and treatment system that can be implemented.

FIG. 4 depicts an example of a system 150 that can be utilized for performing diagnostics and/or treatment of a patient. In some examples, the system 150 can be implemented to generate corresponding maps for a patient's heart 152 in real time as part of a diagnostic procedure (e.g., an electrophysiology study) to help assess the electrical activity and identify arrhythmia drivers for the patient's heart. Additionally or alternatively, the system 150 can be utilized as part of a treatment procedure, such as to help a physician determine parameters for delivering a therapy to the patient (e.g., delivery location, amount and type of therapy) based on one or more identified arrhythmia drivers. For example, a catheter, such as a pacing catheter, having one or more therapy delivery devices 156 affixed thereto can be inserted into a patient's body 154 as to contact the patient's heart 152, endocardially or epicardially. The placement of the therapy delivery device 156 can be guided according to the location of one or more arrhythmia drivers (e.g., stable rotors, foci, fast-firing locations or the like) that have been identified as disclosed herein. The guidance can be automated, semi-automated or be manually implemented based on information provided. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

As a further example, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic) controls. One or more sensors (not shown) can also communicate sensor information back to the therapy system 158. The position of the device 156 relative to the heart 152 can be determined and tracked intraoperatively via an imaging modality (e.g., fluoroscopy, xray), a mapping system 162, direct vision or the like. The location of the device 156 and the therapy parameters thus can be combined to determine corresponding therapy parameter data.

Before, during and/or after delivering a therapy via the therapy system 158, another system or subsystem can be utilized to acquire electrophysiology information for the patient. In the example of FIG. 4, a sensor array 164 includes one or more electrodes that can be utilized for recording patient electrical activity. As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which are incorporated herein by reference. Other arrangements and numbers of sensing electrodes can be used as the sensor array 164. As an example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart.

One or more sensors may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog and/or digital information (e.g., corresponding to electrical data 14).

The control 168 can also be configured to control the data acquisition process (e.g., sample rate, line filtering) for measuring electrical activity and providing the measurement data 170. In some examples, the control 168 can control acquisition of measurement data 170 separately from the therapy system operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

The mapping system 162 is programmed to combine the measurement data 170 corresponding to electrical activity of the heart 152 with geometry data 172 (e.g., corresponding to geometry data 12) by applying appropriate processing and computations to provide corresponding output data 174. The output data 174 can represent or characterize one or more arrhythmia drivers, which can be localized or global drivers across the cardiac envelope (e.g., on a surface of the heart 152).

As an example, the output data 174 can represent one or more arrhythmia drivers (e.g. driver data 30) determined from the electrical measurement data 170 acquired for the patient over various time intervals. As disclosed herein, the arrhythmia drivers can include information characterizing one or more wave front lines (e.g., wave front data 106), one or more rotor core trajectories (e.g., trajectory data 64 or 104), one or more stable rotors (e.g., rotor stability data 102) or a combination of information representing any one or more arrhythmia drivers and/or its derivatives. The output data 174 can include one or more graphical maps demonstrating determined arrhythmia drivers with respect to a geometric surface of the patient's heart 152.

Since the measurement system 166 can measure electrical activity of a predetermined region or the entire heart concurrently (e.g., where the sensor array 164 covers the entire thorax of the patient's body 154), the resulting output data (e.g., visualizing attributes of identified stable rotors and/or other electrocardiographic maps) thus can also represent concurrent data for the predetermined region or the entire heart in a temporally and spatially consistent manner. The time interval for which the output data/maps are computed can be selected based on user input (e.g., selecting a timer interval from one or more waveforms). Additionally or alternatively, the selected intervals can be synchronized with the application of therapy by the therapy system 158.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more). In other examples, the mapping system 162 can compute electrical activity over a sub-region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

Following (or concurrently with) determining electrical potential data (e.g., electrogram data computed from non-invasively and/or invasively acquired measurements) across the geometric surface of the heart 152, the electrogram data can further undergo signal processing to compute one or more cardiac maps. The mapping system 162 can include an automated arrhythmia driver analyzer method 182 for identifying one or more drivers of cardiac arrhythmia, such as disclosed herein (e.g., corresponding to arrhythmia driver analyzer 18). The arrhythmia driver analyzer 182 can also be programmed to compute other characteristics associated with each identified arrhythmia driver, such as including driver sustainability, rotor core trajectories, wave front lines, rotation count for rotors, rotation direction for rotors, angular velocity for rotors, connectivity between rotors, rotor cycle length and related statistics associated therewith.

A map generator 188 can be programmed to generate graphic maps based on the computed output data. Parameters associated with the displayed graphical representation, corresponding to an output visualization of the computed map, such as including selecting a time interval, a type of information that is to be presented in the visualization and the like can be selected in response to a user input via a graphical user interface (GUI) 190. For example, a user can employ the GUI to selectively program one or more parameters (e.g., temporal and spatial thresholds, filter parameters and the like) utilized by the arrhythmia driver analyzer method 182 and/or to select one or more sample time intervals to set a time duration for the electrical data 170. The mapping system 162 thus can generate corresponding output data 174 that can in turn be rendered by the visualization engine 186 as a corresponding graphical output in a display 192, such as including an electrocardiographic map 194. For example, the map generator can generate maps and other output visualizations, such as including but not limited to the maps and other output visualizations disclosed herein.

Additionally, in some examples, the output data 174 can be utilized by the therapy system 158. The control that is implemented can be fully automated control, semi-automated control (partially automated and responsive to a user input) or manual control based on the output data 174. In some examples, the control 160 of the therapy system can utilize the output data to control one or more therapy parameters. As an example, the control 160 can control delivery of ablation therapy to a site of the heart (e.g., epicardial or endocardial wall) based on one or more arrhythmia drivers identified by the arrhythmia driver analyzer method 182. In other examples, an individual can view the map generated in the display to manually control the therapy system. Other types of therapy and devices can also be controlled based on the output data 174 and corresponding graphical map 194.

Figure 5:
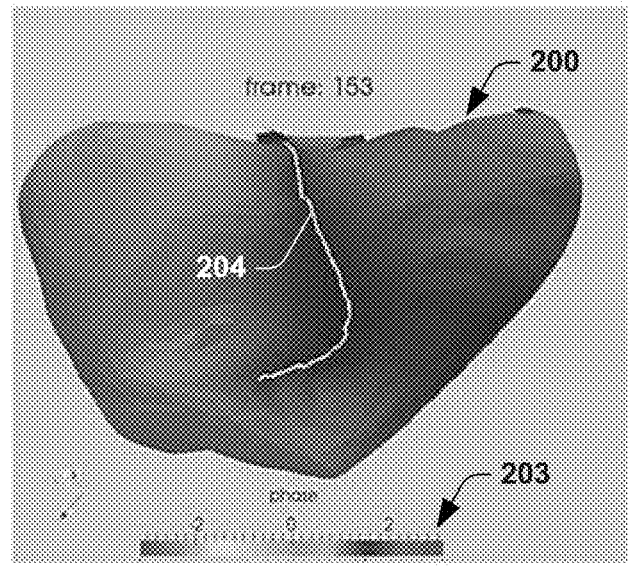
FIG. 5 depicts an example of a graphical map demonstrating a wave front line that can be detected for a time frame.
Figure 6:
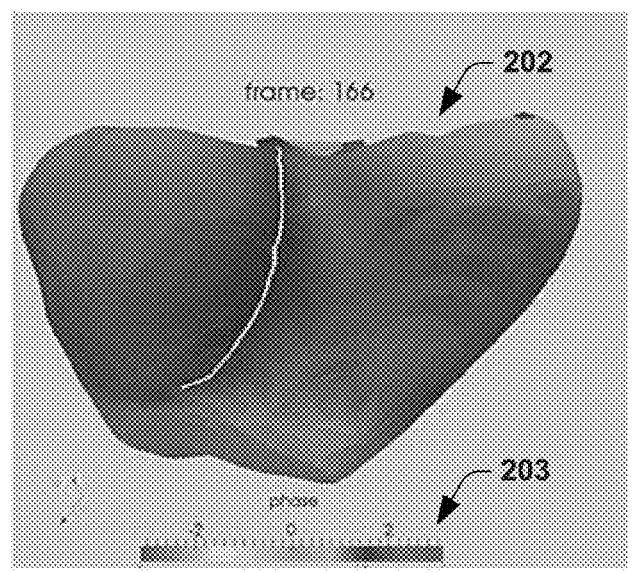
FIG. 6 depicts a graphical map demonstrating another example of a wave front line that can be detected for a different time frame from FIG. 5.

FIGS. 5 and 6 depict examples of graphical maps 200 and 202 of a patient's heart. Each of the graphical maps 200 and 202 demonstrates phase computed (e.g., by phase calculator 16 of FIG. 1) for different time samples from a time interval (e.g., demonstrated at frames 153 and 166). Each of the graphical maps 200 and 202 can include a corresponding phase scale 203 demonstrating a color coding scheme representing values of the computed phase across the surface. Also demonstrated in FIGS. 5 and 6 are wave front lines 204 and 206, respectfully, such as can be computed based upon phase data (e.g., by wave front analyzer 20 of FIG. 1), such as disclosed herein.

Figure 7:
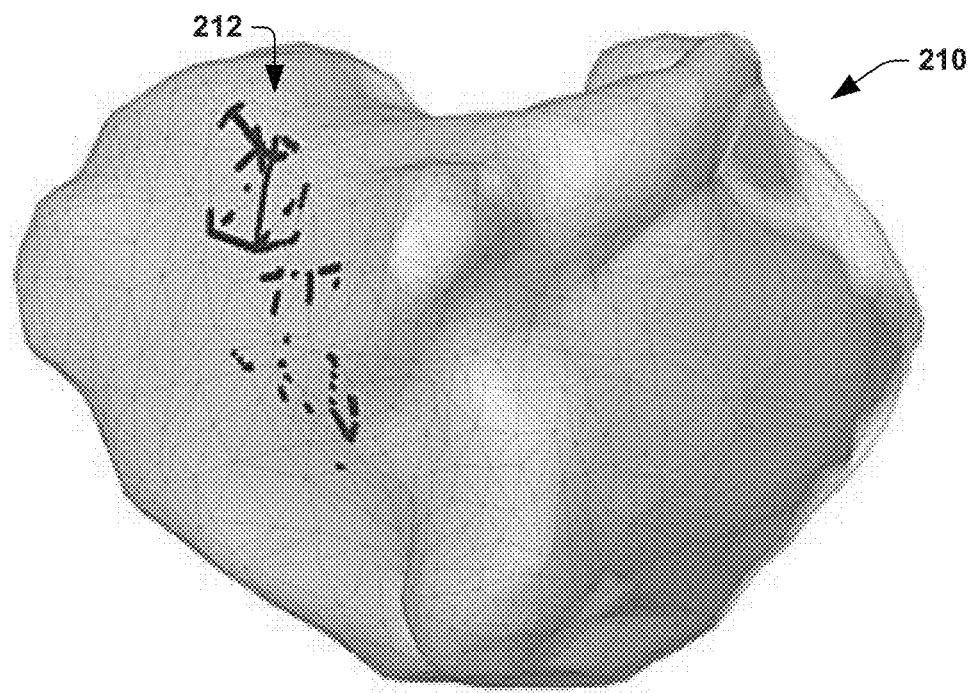
FIG. 7 depicts an example of a graphical map demonstrating wave break points that can be determined.

FIG. 7 depicts a graphical map 210 representing a geometric surface corresponding to an epicardial surface of a patient's heart. The graphical map 210 is demonstrated in a form of a triangular mesh corresponding to the geometric surface, although other types of surface representations could be utilized. The graphical map 210 includes a plurality of wave break points 212, such as can be computed (e.g., by trajectory detector 22 of FIG. 1 or trajectory detector 50 of FIG. 2) based on wave front data generated as disclosed herein.

Figure 8:
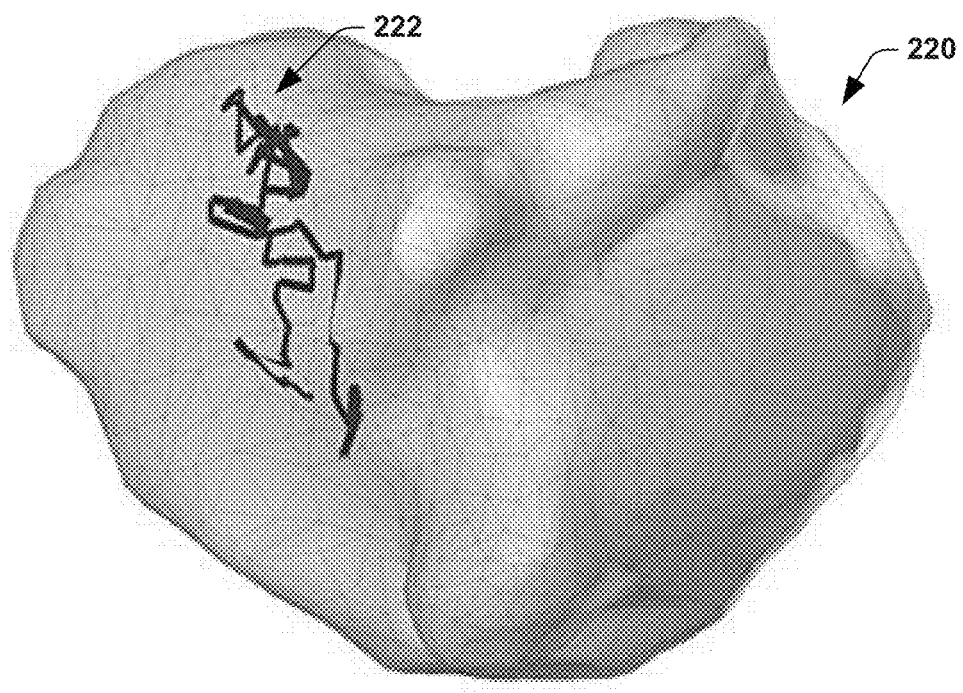
FIG. 8 depicts an example of a trajectory that can be generated from the wave break points of FIG. 7.

In FIG. 8, another graphical map 220 of the geometric surface is illustrated. The graphical map 220 also depicts a rotor core trajectory 222 such as can be computed (e.g., by trajectory detector 22 of FIG. 1 or detector 50 of FIG. 2) based upon the wave break points 212 of FIG. 7. The rotor core trajectory 222 thus provides a path across the geometric surface corresponding to the travel of a rotor core over a plurality of time samples.

FIGS. 9A, 9B, 9C and 9D depict examples of different types of stable rotor maps 230, 232, 234 and 236, respectively that can be generated (e.g., by map generator 32 of FIG. 1 or mapping system 162 of FIG. 2). In each map 230, 232, 234 and 236, at least two stable rotors 240, 241 and 242 are identified based on stable portion(s) of rotors.

By way of example, the graphical map 230 demonstrates a phase map that can be generated based on phase data computed (e.g., by phase calculator 16 of FIG. 1) based on electrical or electrical anatomical data. For example, the stable rotor map 230 in FIG. 9A can be created and represent a duration of rotations at each location according to a corresponding color scale (e.g., darker color denoting a longer duration of rotations for each identified rotor 240, 241 and 242. In FIG. 9B, the map includes a graphical representation of a rotor core trajectory 246 distributed across the geometric surface and overlaid on the rotor duration map of FIG. 9A. The trajectory 246 can be computed based on the phase information demonstrated in FIG. 9A over a plurality of time samples. As demonstrated, the trajectory may wander beyond a prescribed spatial threshold from the centroid (e.g., 2 cm diameter), but only the portion that was stable is used to create the map.

The graphical map 234 in FIG. 9C includes an indication of the number of rotations for each of a plurality of stable rotor portions 240, 241 and 242. For example, the graphical map 234 includes indicators presented at centers of stable rotor portions indicating a computed number of rotations for each respective stable portion. In FIG. 9D, the graphical map 236 includes an aggregation of the information presented in each of the respective maps 230, 232 and 234 and a visualization of other trajectories 248 that do not include any stable portion, demonstrated at 248. For instance the map 236 demonstrates stable rotors, overlaid with stable rotor trajectory 246, long lasting trajectories without any stable portion 248 and number of rotation for stable rotors. Thus is understood that the map generator and mapping system can provide individual information that can be generated by the phase calculator and arrhythmia driver analysis as well as aggregate information from different portions thereof. Thus it is to be appreciated that graphical maps generated can include graphical data representing one or more derived characteristics such as including phase information and rotor analysis data.

Figure 10:
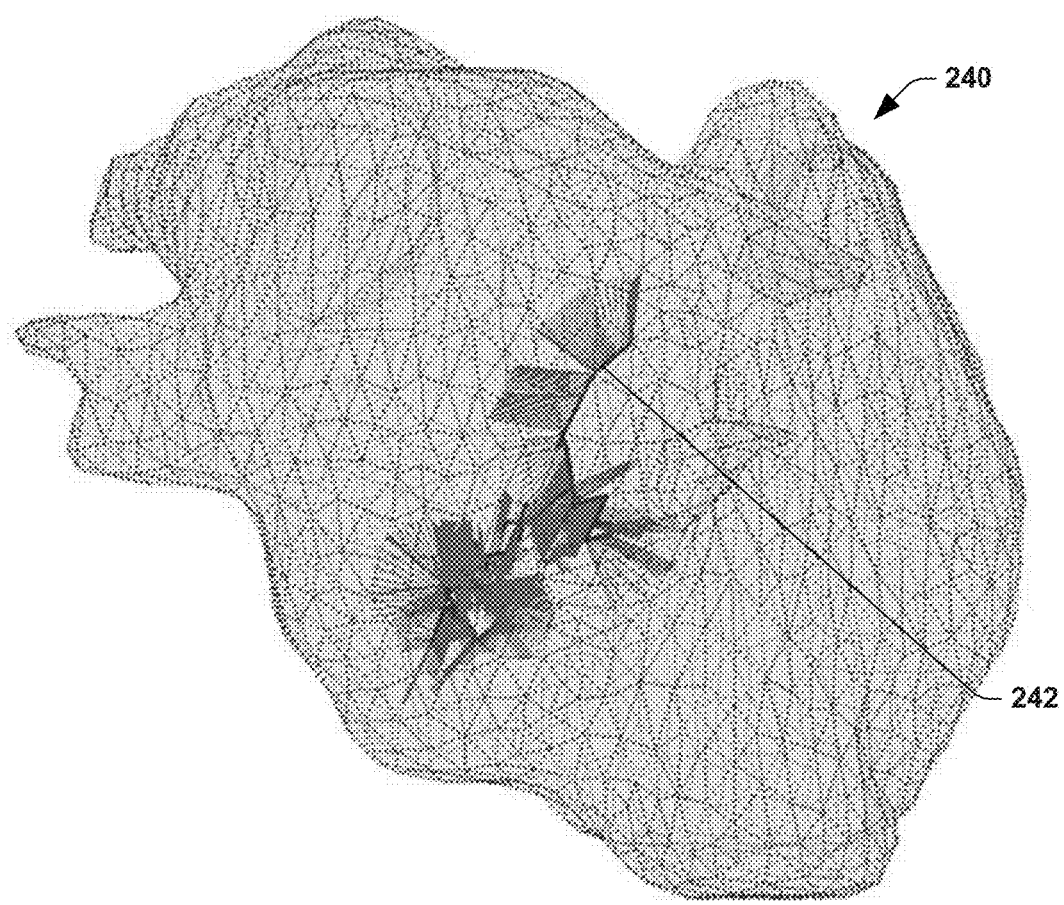
FIG. 10 demonstrates an example of a rotor core trajectory and associated wave front directions along a trajectory.

FIG. 10 depicts an example of a graphical map 240 of a surface geometry in the form of triangular mesh structure corresponding to the surface. In the example map 240, a rotor core trajectory 242 is demonstrated across the surface such as can be detected by a trajectory detector as disclosed herein. Additionally, wave front directions can be computed (e.g., by a wave front analyzer 20 of FIG. 1) are also demonstrated along the computed trajectory.

Figure 11:
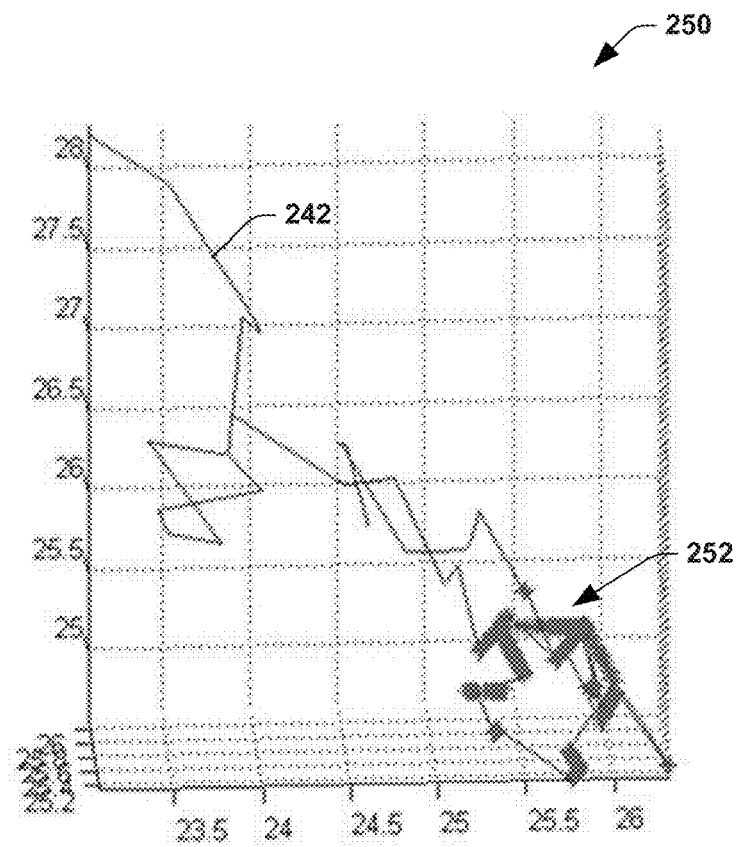
FIG. 11 depicts the same trajectory from FIG. 10, and its stable portion demonstrated via markers along the trajectory.

FIG. 11 depicts an example of the same trajectory 242 from FIG. 10 demonstrated in a three-dimensional plot such as corresponding to the coordinate system corresponding to a geometric surface of the patient's anatomy. Also demonstrated at 252 in FIG. 11 is a corresponding stable rotor portion as denoted by asterisks along the portion of the rotor core trajectory determined to be stable (e.g., by stability detector 24 of FIG. 1 or stability detector 100 of FIG. 3).

Figure 12:
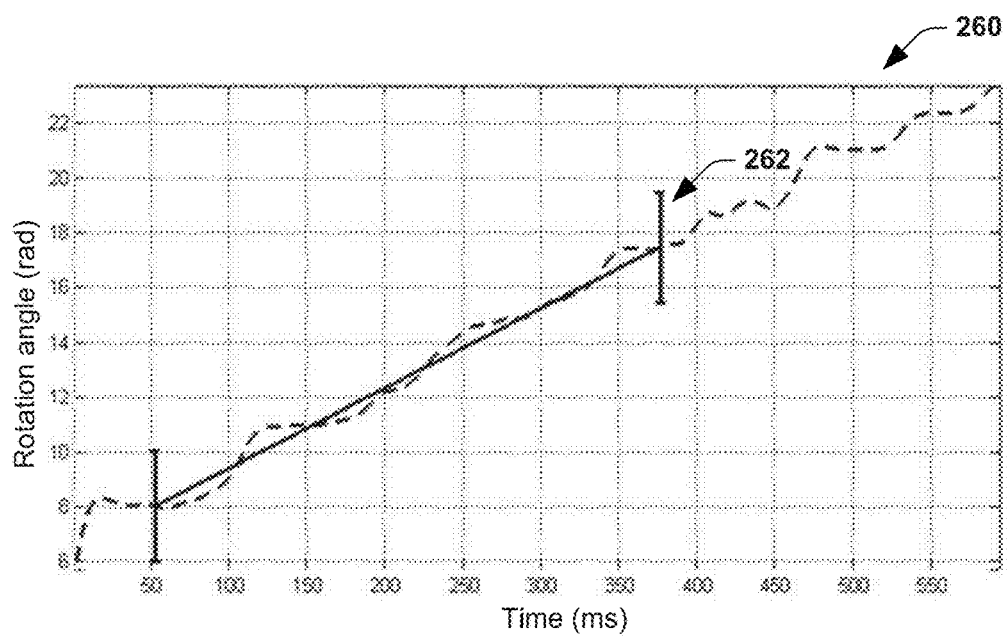
FIG. 12 depicts an example of a graph of rotation angle demonstrating unwrapped angles for the trajectory of a rotor core.

FIG. 12 depicts an example of a graph 260 of rotation angle (in radians) as a function of time (in milliseconds). In the example of FIG. 12, the rotation angle is unwrapped to show a continuous variation in rotation angle over time. The stable portion of the rotor 252 of FIG. 11 is also demonstrated between calipers 262. From FIG. 12, it can be determined that the stable rotor count for the stable portion 262 is about 1.5 rotations out of a total of about 2.8 overall rotations during the time interval. Additionally, the stable portion of the rotor has a rotation cycle of about 212 milliseconds (ranging from about 52 milliseconds to about 364 milliseconds). As disclosed herein, a given rotor trajectory can include one or more stable portions each of which can be separately analyzed such as by determining rotor statistics (e.g., by rotor statistics calculator 26 of FIG. 1).

Figure 13:
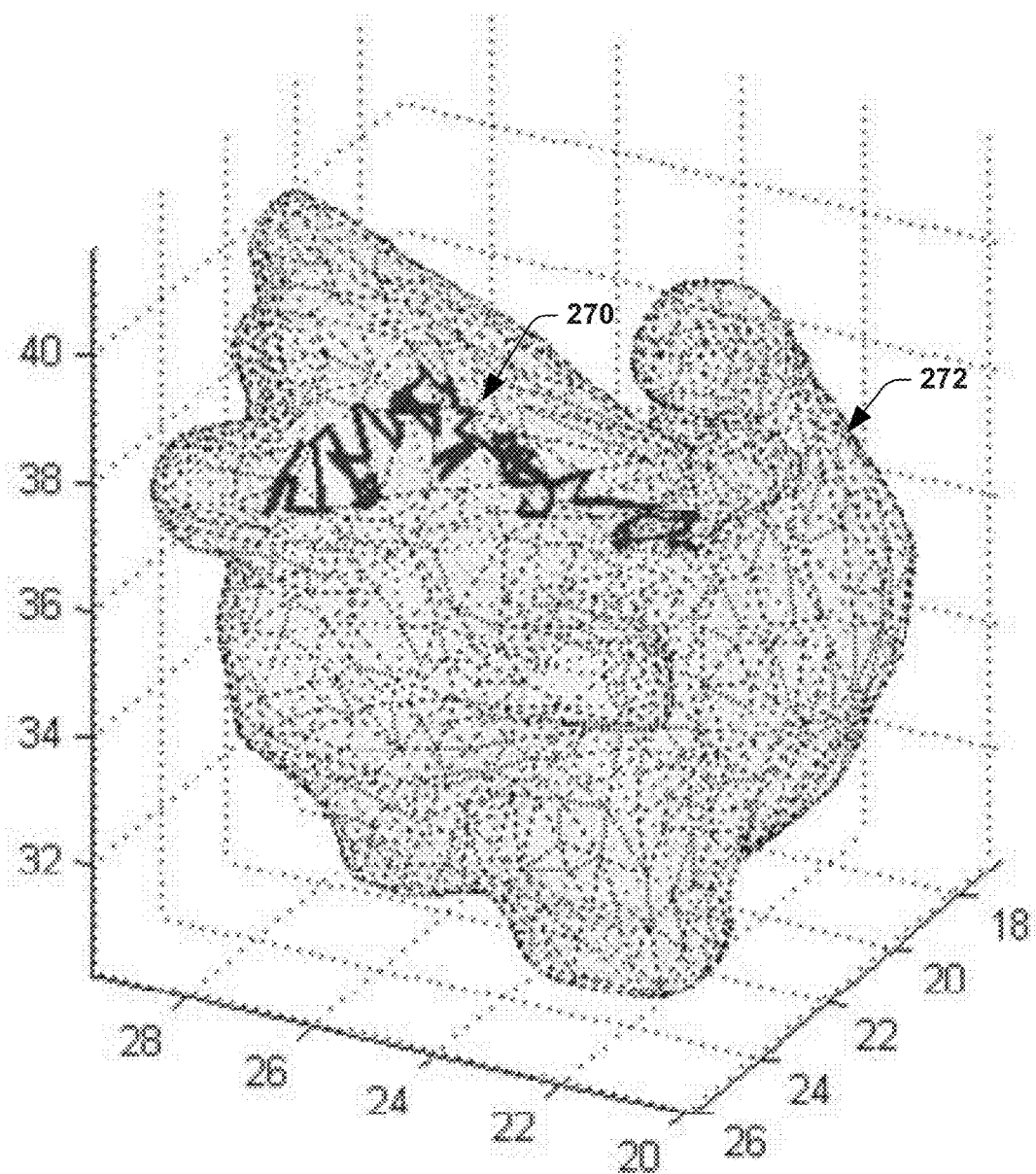
FIG. 13 depicts an example of a graph demonstrating rotor core trajectory with that can be generated based on electrical data acquired for a given patient.

By way of further example, FIGS. 13-19 depict examples of analysis that can be performed (e.g., by arrhythmia driver analyzer 18 or 182) with respect to a rotor core trajectory. In the example of FIG. 13, a rotor core trajectory 270 can be determined based on wave front data generated across a geometric surface, such as geometry of an epicardial surface of a patient's heart 272. The trajectory thus can be represented in three-dimensional space as a path of travel along the surface 272 such as can be determined as disclosed herein.

Figure 14:
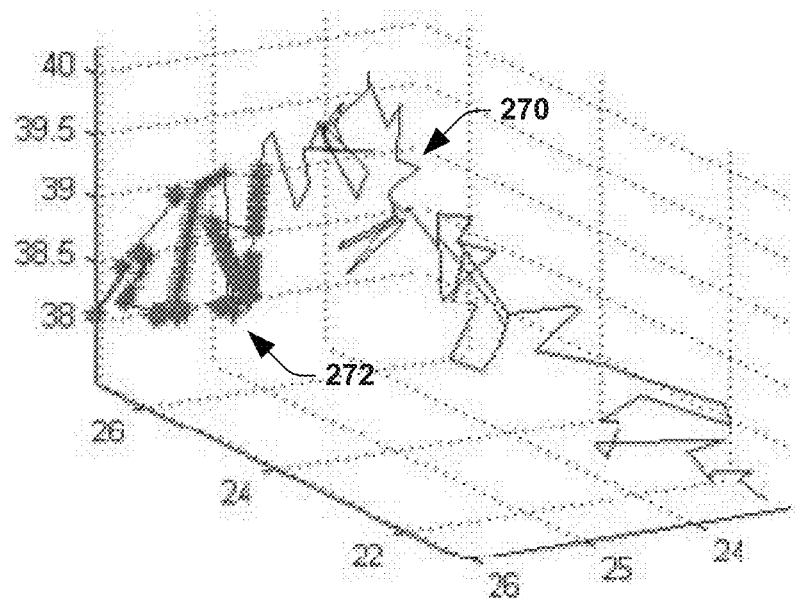
FIG. 14 depicts a plot of the trajectory from FIG. 13 demonstrating a first stable rotor portion.
Figure 15:
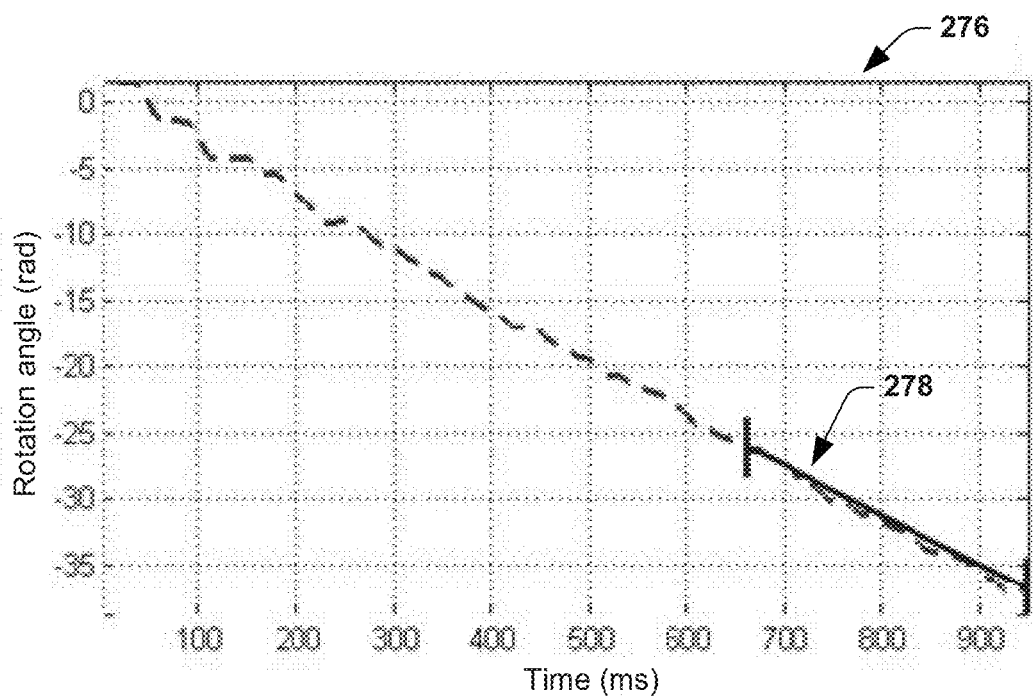
FIG. 15 depicts a graph of corresponding rotation angles for the trajectory of FIG. 14.

FIG. 14 demonstrates the rotor core trajectory 270 plotted in three-dimensional space in which a first stable portion 272 can be detected (e.g., by stability detector 24 or 100). FIG. 15 demonstrates a graph 276 of a rotation angle as a function of time for the trajectory 270. The first stable portion 270 of FIG. 14 is demonstrated at 278, and contains about 1.7 rotations of about six total separate discrete rotations that can be ascertained from the electrical data acquired for the given patient.

Figure 16:
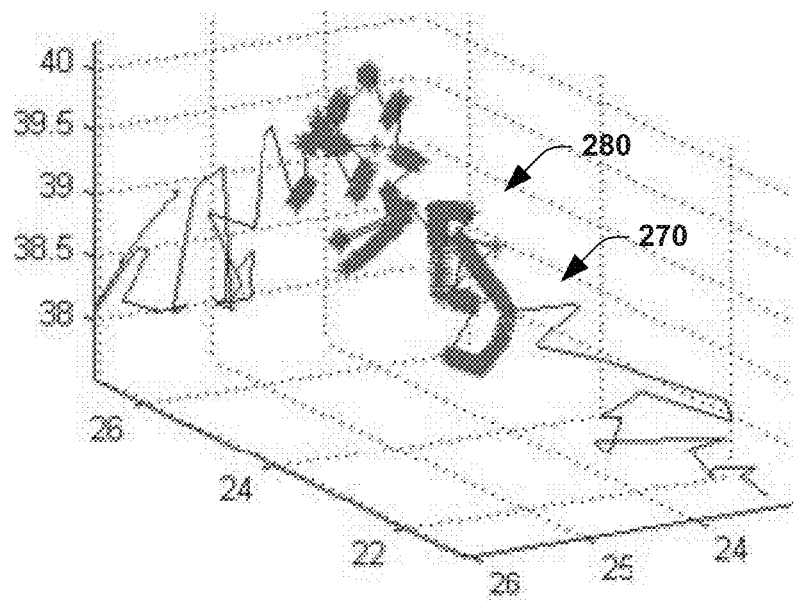
FIG. 16 depicts a plot of the trajectory from FIG. 13 demonstrating a second spatially stable portion.
Figure 17:
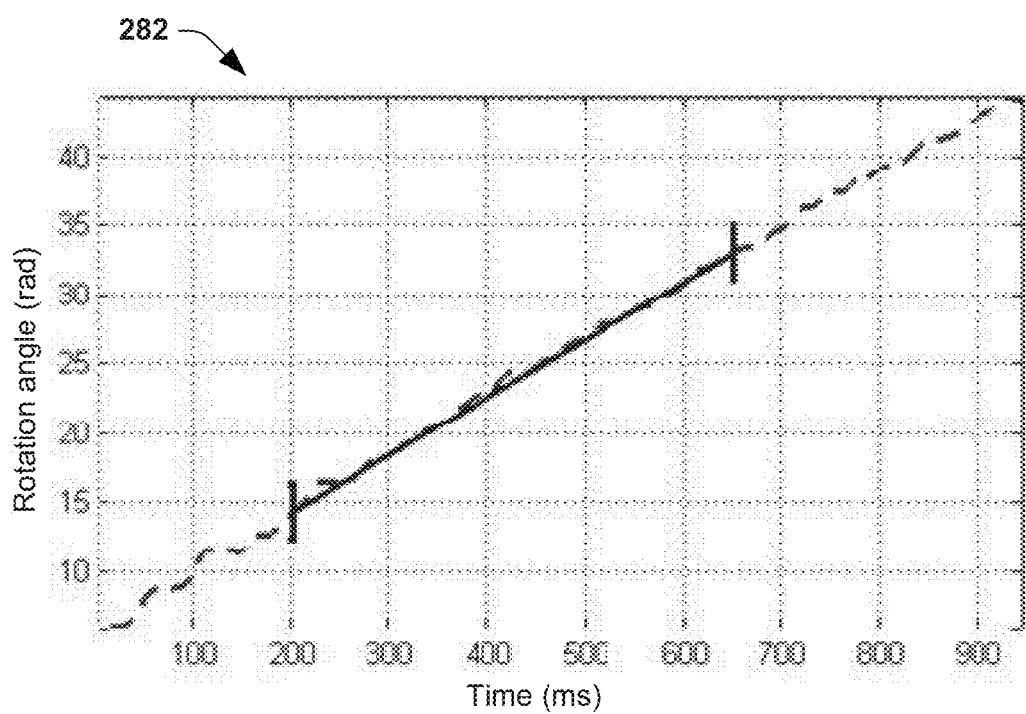
FIG. 17 depicts a graph of corresponding rotation angles for the trajectory of FIG. 16.

FIG. 16 demonstrates a three-dimensional plot of the trajectory 270 and includes a separate stable portion demonstrated at 280. FIG. 17 a graph 282 of the rotation angle for the second stable portion 280 of FIG. 16. In the example of FIG. 17 the rotation angle for the stable portion of the rotor increases from about 200 milliseconds to about 650 milliseconds, containing about three stable angular rotations for the rotor along such trajectories.

Figure 18:
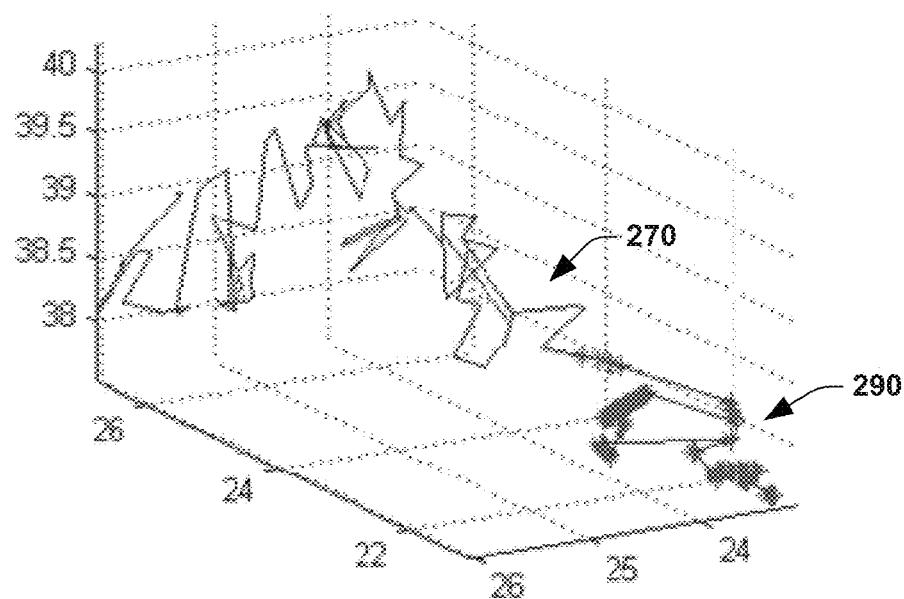
FIG. 18 depicts a plot of the trajectory from FIG. 13 demonstrating a third spatially stable portion.
Figure 19:
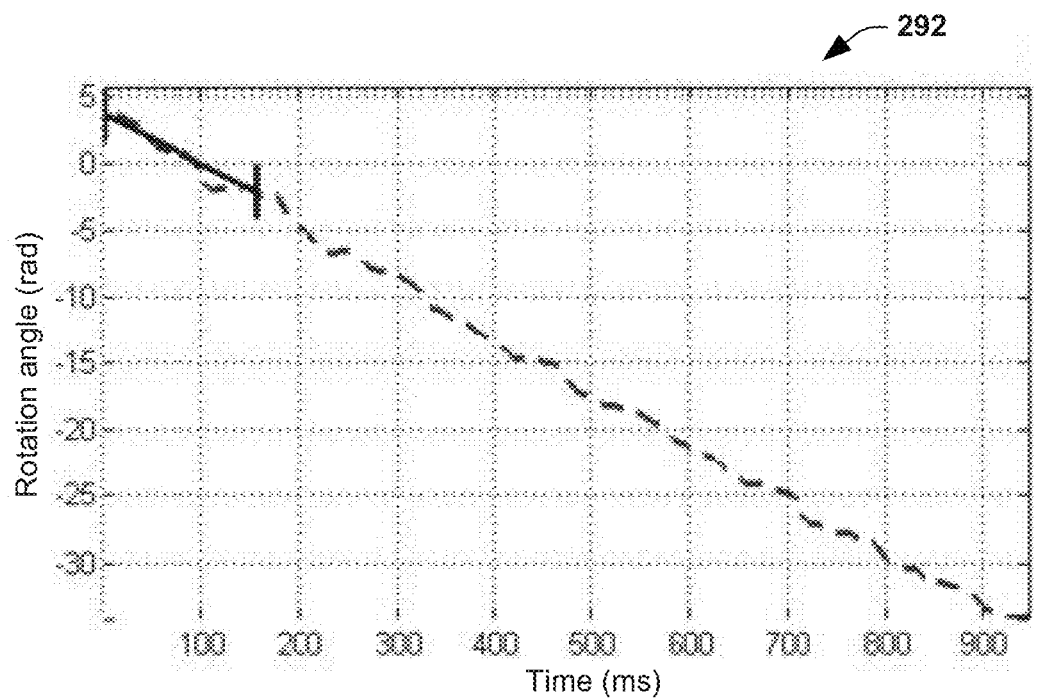
FIG. 19 depicts a graph of corresponding rotation angles for the trajectory of FIG. 18.

FIG. 18 demonstrates another example of the rotor core trajectory 270 and includes a third stable portion thereof, demonstrated at 290. The third stable portion has a decreasing angular rotation (e.g., negative rotation) compared with respect to the angular rotation of FIG. 17 and exists from about 0 milliseconds to about 160 milliseconds. FIG. 19 demonstrates a graph 292 of a rotation angle as a function of time for the trajectory 270, including the third stable portion of the trajectory. The rotation angle contains about 0.9 rotations for the stable portion 290 of FIG. 18. In addition to ascertaining the rotation angle for each stable portion, as disclosed herein, other statistics can also be computed, which can include an angular rotation rate, angular acceleration or the like for each rotor as well average mean, standard deviations and other related statistics for the rotation angle. The number of rotations can also be computed as well as the direction rotation for each of the stable portions that might exist in a given rotor trajectory.

Figure 20:
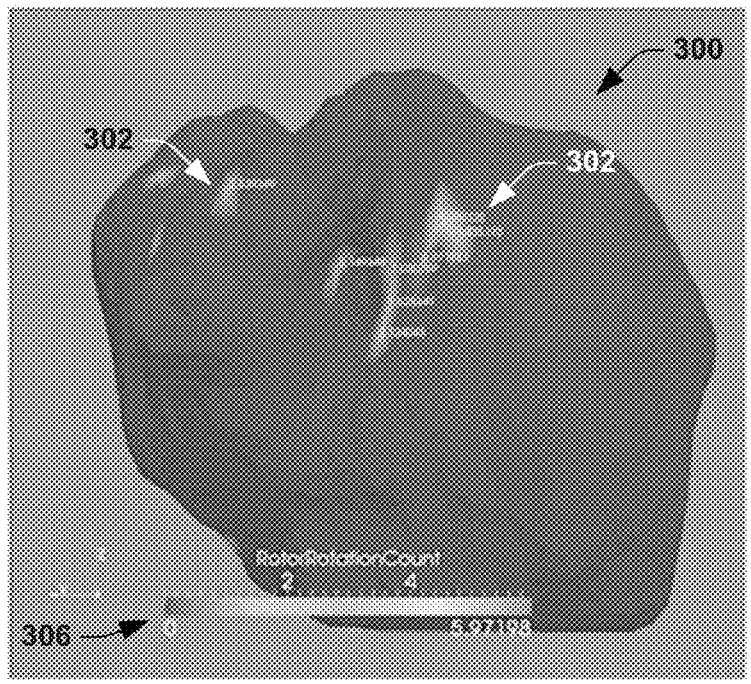
FIG. 20 depicts an example of a graphical map demonstrating automatic rotation counts generated for stable rotors based on electrical data acquired for a given patient.

FIG. 20 depicts an example of a graphical map 300 for a portion of a patient's anatomy demonstrating a count of rotor rotation across the geometric surface, such as can be computed from arrhythmia driver data. Regions having an increased rotor rotation count are graphically differentiated according to a color coded scale 306. Each of the graphical regions of increased rotation counts are graphically demonstrated at 302.

Figure 21:
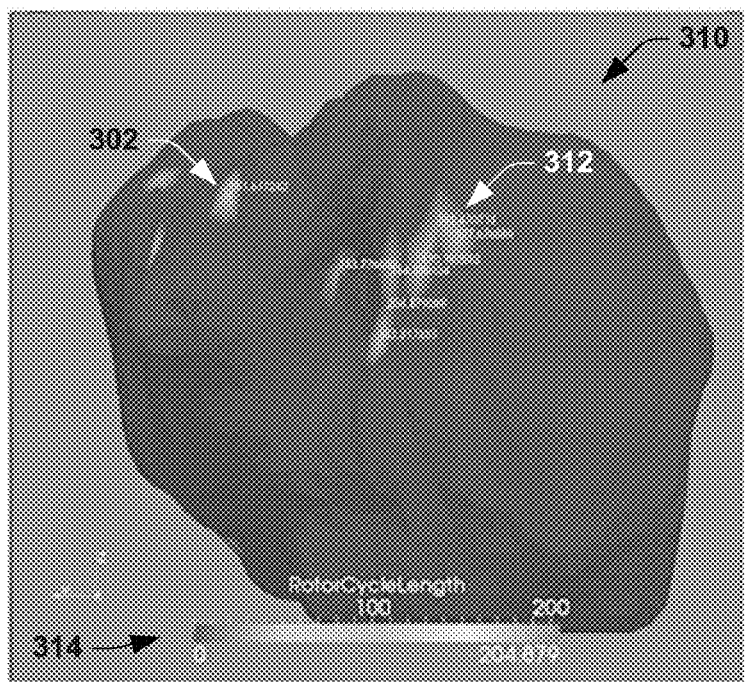
FIG. 21 depicts an example of a graphical map demonstrating automatic rotation cycle length generated for stable rotors based on electrical data acquired for a given patient.

FIG. 21 demonstrates an example of another graphical map 310 in which rotor cycle length is computed and demonstrated on the graphical map at 312, according to a corresponding scale 314. Regions of rotor cycle length thus can be computed by the stability detector or rotor statistics methods that can be implemented as disclosed herein. In addition to graphically demonstrated the cycle length according to the scale 314 the computed cycle length for a given region of interest across the surface of the graphical can also be plotted and depicted on the map itself.

Figure 22A:
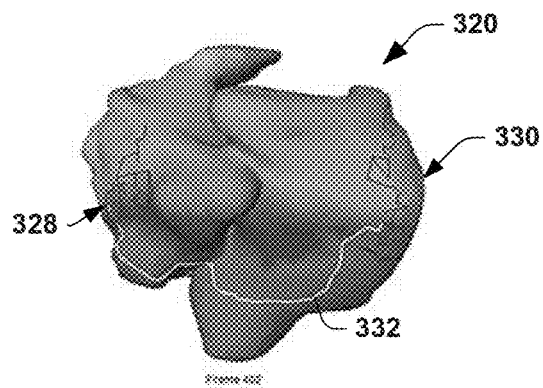
FIGS. 22A, 22B, 22C and 22D depict examples of stable rotor pairs for different time frames.
Figure 22B:
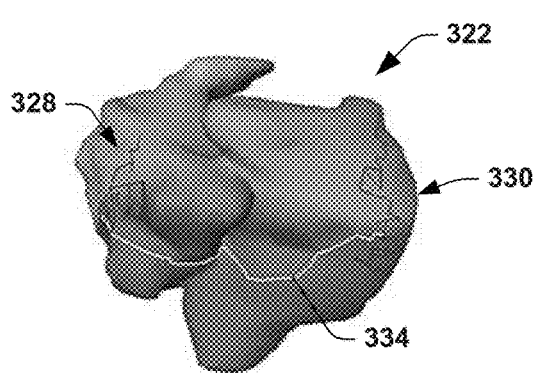
Figure 22C:
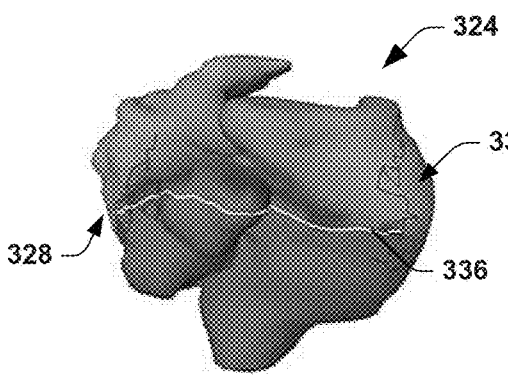
Figure 22D:
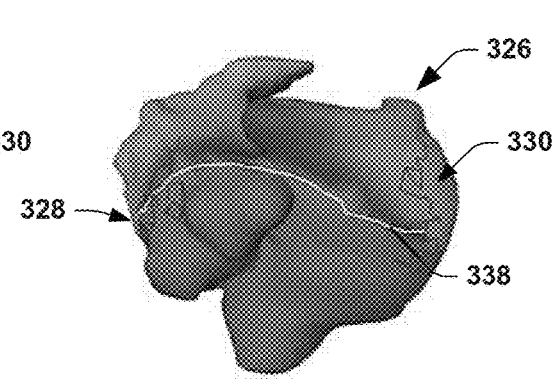

As disclosed herein, a pair of stable rotor cores may exhibit connectivity, which can be ascertained by a rotor connectivity function (e.g., connectivity function 28 of FIG. 1). By way of illustration, FIGS. 22A, 22B, 22C and 22D demonstrate an example of how rotor connectivity can be determined. Each of these FIGS. 22A, 22B, 22C and 22D include graphical maps 320, 322, 324, and 326, respectfully, for a corresponding geometric surface of a patient's heart. In each of the graphical maps 320-326 corresponding rotor trajectories can be computed and plotted thereon, demonstrated at 328 and 330 in each of the respective maps. That is, the trajectories in each of the respective maps are the same trajectory that can be computed by trajectory detector as disclosed herein. Since each of these maps represent a different time frame, a corresponding wave front line can also be plotted on the map and, if connectivity exists, extend between each of the trajectories 328 and 330 for each map. For example, in FIG. 22A, a wave front line 332 connects between corresponding wave break points in each of the trajectories 328 and 330. Similarly wave front lines 334, 336 and 338 connect to respective wave break points in each of the corresponding trajectories 328 and 330 for each of the respective time frames. By determining that wave front lines connect between corresponding wave break points along a pair of trajectories, for at least a threshold amount of time, the systems and methods disclosed herein can ascertain that the stable portions of such trajectories that contain the wave break point pairs are likewise connected by wave front lines.

Figure 23:
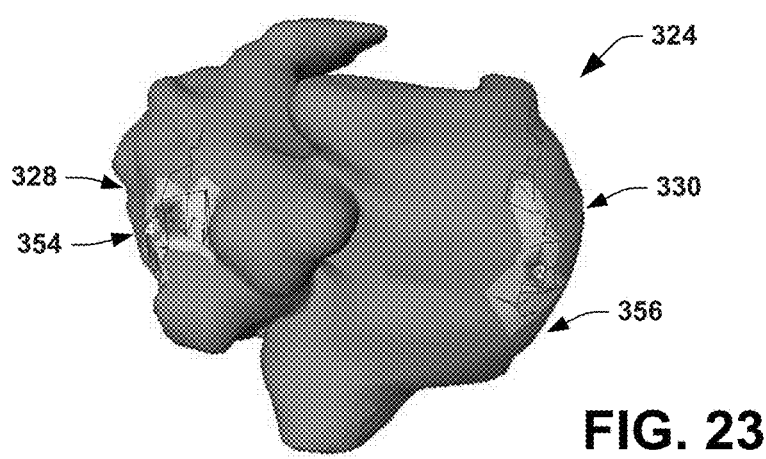
FIG. 23 depicts an example of a graphical map demonstrating the overall trajectory and rotor stability for a pair of linked stable rotors.

FIG. 23 depicts an example of a graphical map 350 in which the corresponding stable rotor portions 352 and 354 have been identified (e.g., by connectivity function 28 of FIG. 1) along the corresponding trajectories 328 and 330 based on determining a sufficient level of connectivity by wave front lines as disclosed herein. Additionally as demonstrated in FIG. 23, a count indicating the number of angular rotations for each respective stable rotor portions 354 and 356 can be superimposed (e.g., overlaid) on the stable rotor portion, demonstrated as 4 and 2, respectively.

Figure 24:
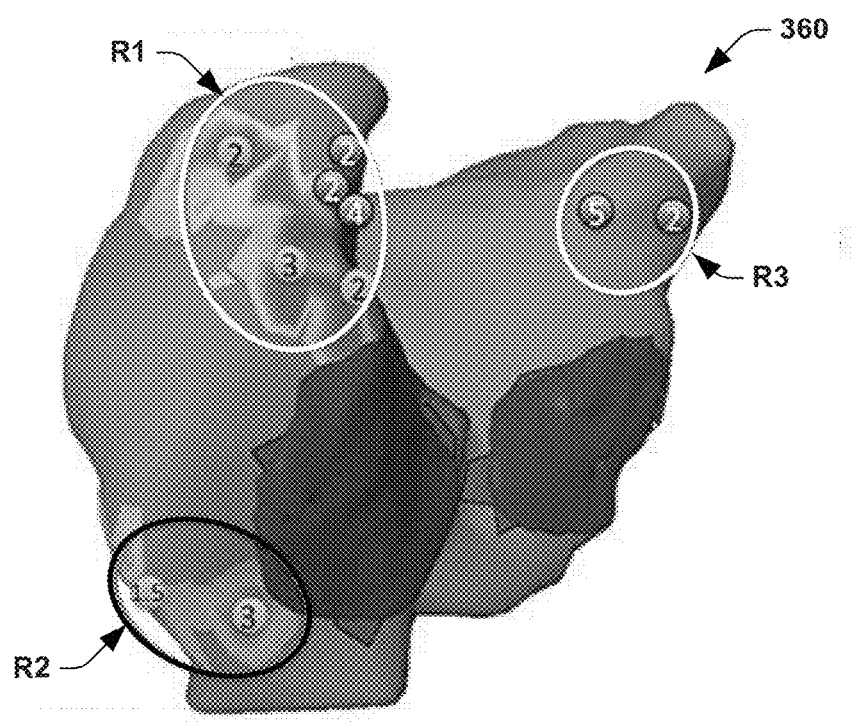
FIG. 24 depicts an example of a graphical map demonstrating an indication of sustainability for arrhythmia drivers for a plurality of regions.

FIG. 24 depicts an example of a graphical map 360 that can be generated to demonstrate sustainability computed for one or more arrhythmia drivers across a geometric surface associated with patient anatomy (e.g., the heart). In the example of FIG. 24, the map includes a plurality of regions R1, R2 and R3 across the surface. Each of the regions R1, R2 and R3 can correspond to designated regions of interest, such as predetermined anatomical regions, automatically selected based on detecting multiple arrhythmia drivers in each region or be selected in response to a user input. Within each of the regions, for each detected arrhythmia driver (e.g., each rotor or focal discharge), a count of events can be determined and presented in each region. For example, during a selected time interval, region R1 includes three rotors having 2, 3 and 2 rotations, respectively, and three foci having 2, 2, and 4 focal discharges, respectively. Region R2 has two rotors having 1.5 and 3 rotations, respectively, during the selected time interval, and Region R3 has two foci with 5 and 2 discharges, respectively, during the selected time interval.

By way of example, for each region, an index or multiple indices can be computed to provide an indication of sustainability for one or more arrhythmia drivers. Each of the indices can be computed based on a number of an average number identified arrhythmia driving events that occur for a given type of driver per region. For the example of rotor sustainability, the index can be computed as in Eq. 1 herein. For the example of focal sustainability (e.g., the number of a focal source discharges from a given anatomical location, over a time interval), the index can be computed as follows:

$$\text{Foci Sustainability} = \frac{\Sigma \text{ focal discharges}}{\Sigma \text{ intervals where occurred}} \qquad \text{Eq. 2}$$

Other indices for other arrhythmia drivers could also be computed. Each of the computed indices can be combined to represent an aggregate degree of driver sustainability for a selected region, such as locally (e.g., for an anatomical location) or globally across the entire surface. The aggregate sustainability index can for the selected region can be determined as follows:

Driver Sustainability=Σ(Rotor Sustainability+Foci Sustainability)     Eq. 3

Continuing with the example of FIG. 24, indices can be computed as follows:

Sustainability for Region 1 (R1):

$$\text{Rotor Sustainability}_{R1} = \frac{7 \text{ rotations}}{3 \text{ detections}} = 2.33$$

$$\text{Foci Sustainability}_{R1} = \frac{8 \text{ focal discharges}}{3 \text{ interval occurrences}} = 2.67$$

$$R1 \text{ Driver Sustainability}_{R1} = \frac{15}{6} = 2.5$$

Sustainability for Region 2 (R2):

$$\text{Rotor Sustainability}_{R2} = \frac{4.5 \text{ rotations}}{2 \text{ detections}} = 2.25$$

$$\text{Foci Sustainability}_{R1} = NA$$

$$R2 \text{ Driver Sustainability}_{R2} = \frac{4.5}{2} = 2.25$$

Sustainability for Region 3 (R3):

$$Rotors_{R3} = NA$$

$$Foci_{R3} = \frac{7 \text{ focal discharges}}{2 \text{ interval occurrences}} = 3.5$$

$$R3 \text{ Driver Sustainability}_{R3} = \frac{7}{2} = 3.5$$

Aggregate driver sustainability:

$$\text{Driver Sustainability} = \frac{\sum_{n=R1}^{R3} \text{Rotor rotations} + \text{focal discharges}}{\sum_{n=R1}^{R3} \text{Rotor occurences} + \text{Foci interval ocurrences}}$$

$$= \frac{26.5}{10}$$

$$= 2.65$$

As used herein, each of the regional and aggregate sustainability indices computed (e.g., by arrhythmia analyzer 18 or 182) can be utilized to control targeted delivery of treatment (e.g., by therapy system 258).

Figure 25:
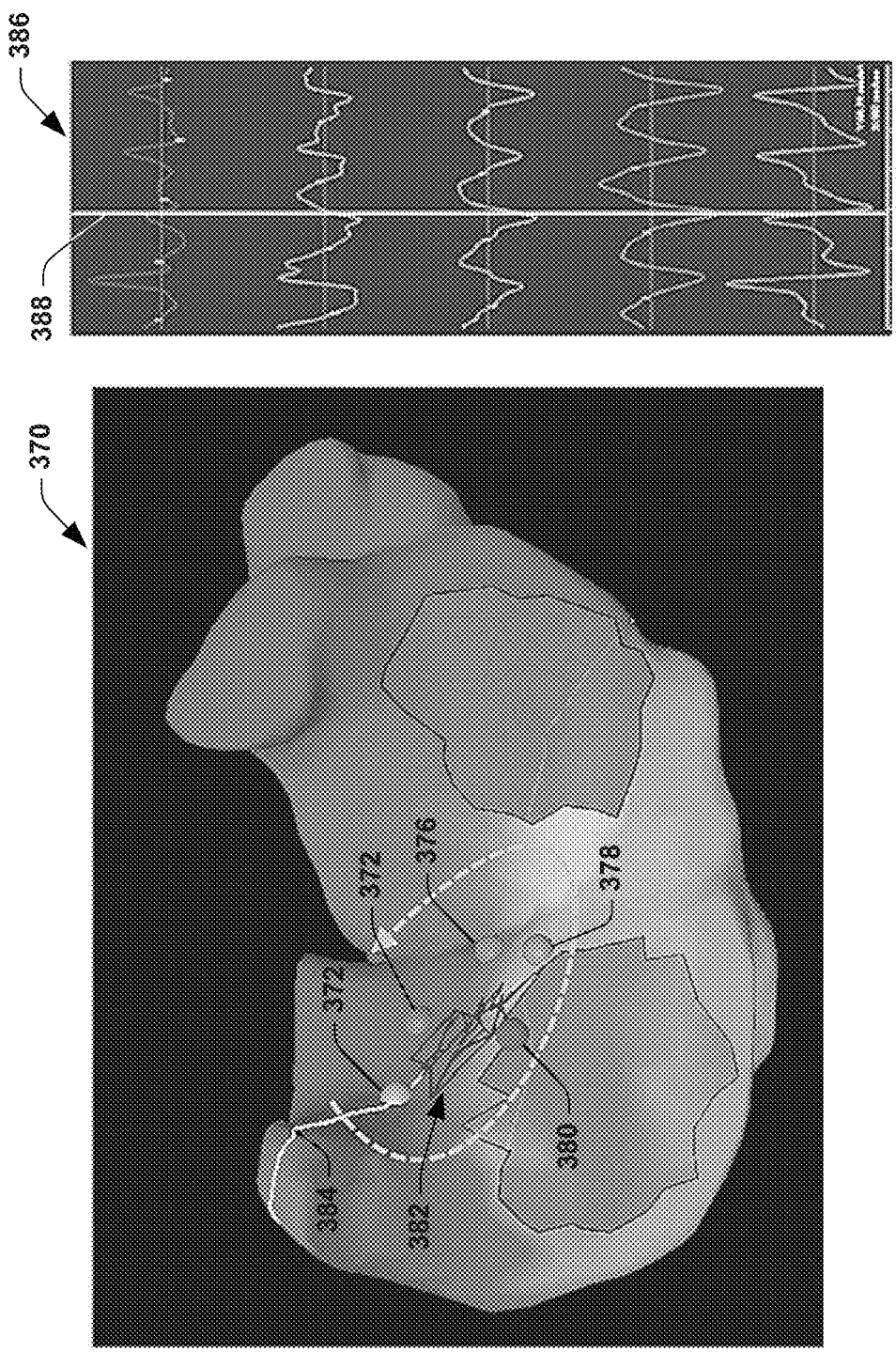
FIG. 25 depicts an example of a graphical map demonstrating electrical activity of nodes surrounding a stable rotor.

FIG. 25 demonstrates a graphical map 370 of the heart that includes a plurality of locations 372, 374, 376, 378 and 380 that have been selectively placed around a counter-clockwise rotating stable rotor, demonstrated at 382 rotating in the direction of the dashed arrow. The locations 372, 374, 376, 378 and 380 can be populated on the map 370 around the stable rotor automatically or in response to a user input. The stable rotor 382 can be detected (e.g., by stability detector 24 or 100) based on the approach disclosed herein. The line segments are the rotor core trajectory 380, while the line 384 extending from the rotor core trajectory through virtual electrode 372 corresponds to the wave front line rotating around rotor core (e.g., determined by wave front analyzer 20). FIG. 25 also demonstrates a set of rotor waveforms (e.g., electrograms) 386 displayed concurrently with the graphical map (e.g., in the same or in another window). The waveforms 386 can correspond to the electrical activity at each of the selected locations 372, 374, 376, 378 and 380 positioned around the rotor core 382. In the waveforms an activation time can be marked, such as by line 388. The rotor waveforms and waveforms surrounding each rotor can be further analyzed (e.g., by arrhythmia driver analyzer 18) to determine the quality of the rotor.

Figure 26:
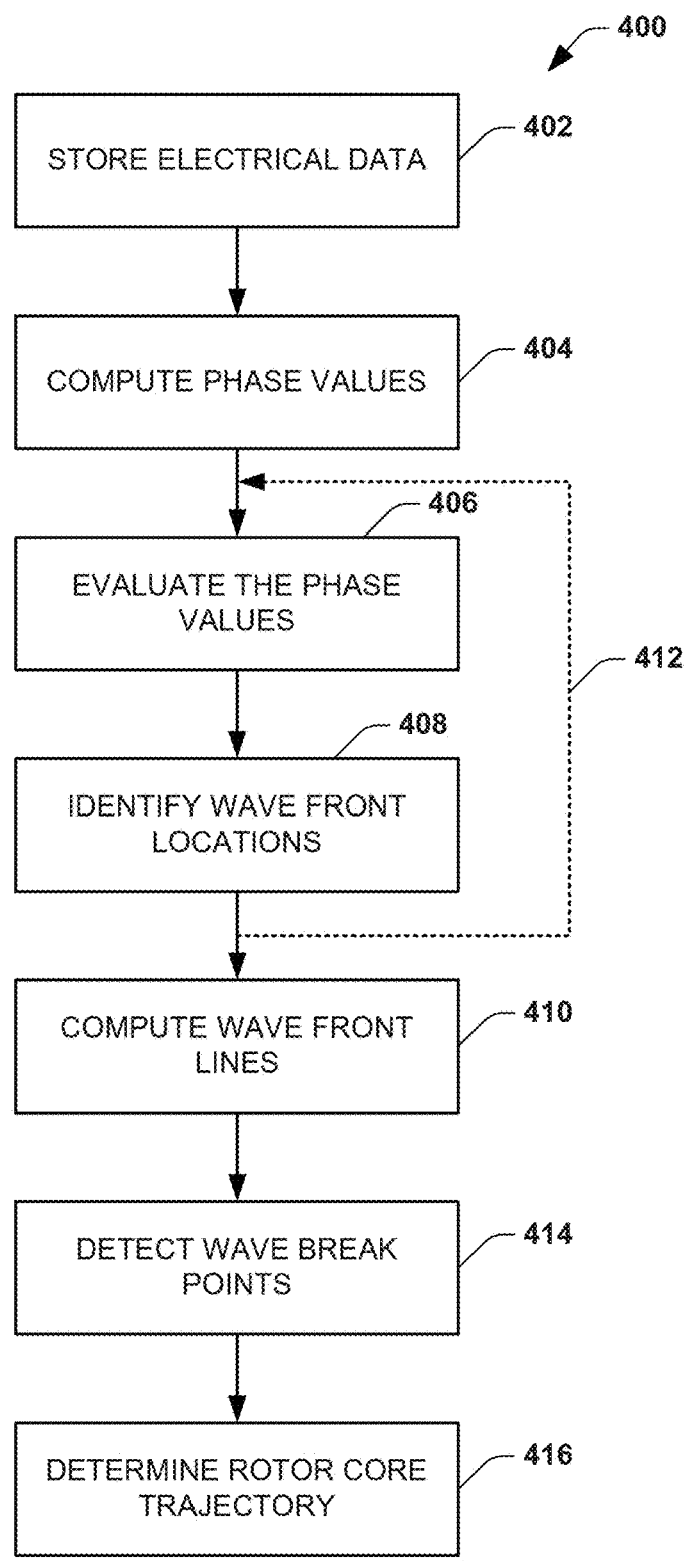
FIG. 26 is a flow diagram depicting an example of a method for analyzing and detecting arrhythmia drivers.
Figure 27:
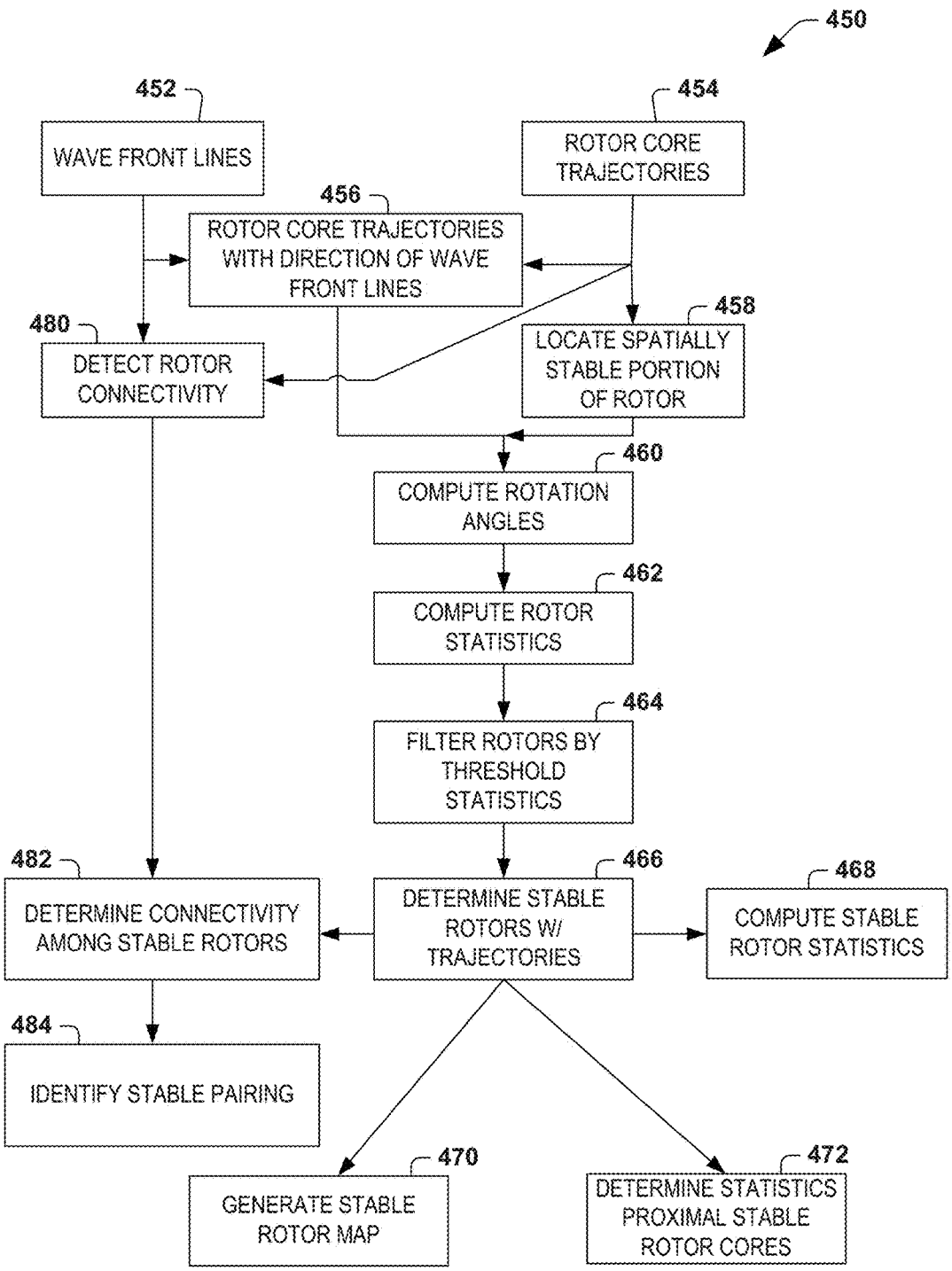
FIG. 27 depicts an example of a method for detecting stable rotors and generating related information.

In view of the foregoing structural and functional features described above, a method that can be implemented will be better appreciated with reference to FIGS. 26 and 27. While, for purposes of simplicity of explanation, the methods of FIGS. 26 and 27 are shown and described as executing serially, it is to be understood and appreciated that such method is not limited by the illustrated order, as some aspects could, in other embodiments, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource (e.g., one or more processor cores) of a computer system, for example.

FIG. 26 is a flow diagram depicting an example method 400 that can be utilized to determine rotor core trajectory such as disclosed herein. At 402, electrical data for a plurality of time samples over one or more time intervals (e.g., each interval containing any number of time samples) can be stored in memory. At 404, phase values can be computed (e.g., by phase calculator 16) based on the stored electrical data for each of a plurality of nodes distributed across a geometric surface. As disclosed herein, in some examples such as where the electrical data has been reconstructed from measurements to include phase information for an entire surface of the heart, most of the electrical phase data computed at 404 can represent phase for more than one chamber and, in some examples, spatially and temporally consistent phase data for the entire surface of the patient's heart.

At 406, the computed phase values can be evaluated and at 408 wave front locations can be identified (e.g., by wave front analyzer 20). At 410, wave front lines can be computed based on the identified wave front locations. The process of evaluating a phase data and identifying wave front locations can be repeated across the entire geometric surface based upon the phase data that has been computed over the plurality of time samples.

At 414, wave break points can be detected (e.g., by trajectory detector 22 or 50) for each of the wave front lines that have been identified in each of the respective time samples. Each detected wave break point thus can be time indexed according to the respective time sample in which the corresponding wave front line has been identified. At 416 rotor core trajectory can be determined from the wave break points that have been detected (at 414), such as disclosed herein with respect to the trajectory detector 50 of FIG. 2. Each rotor core trajectory determined at 416 can be stored in memory as trajectory data (e.g., data 64 or 104) for use further processing and/or generating a graphical map, such as disclosed herein.

FIG. 27 is a flow diagram demonstrating an example of a method 450 that can be utilized for detecting and analyzing stable rotors. At 452, wave front lines have been determined and stored in memory as wave front data (e.g., wave front data 52 of FIG. 2). Additionally, rotor core trajectories can be stored in memory at 454. At 456, rotor core trajectories can be ascertained in conjunction with the direction of the wave front lines based upon the wave front lines (provided at 452) and rotor core trajectories (provided at 454) that have been determined over time.

At 458, spatially stable portions of the rotor can be located based upon the determined rotor core trajectories (e.g., by stability detector 24 of FIG. 1 or spatial analysis 108 of stability detector 100 of FIG. 3). For example, the spatially stable portion rotor can be detected based upon applying initial temporal and spatial constraints to the rotor core trajectory data.

For each spatially stable portion (e.g., having sufficient duration and length over time) rotation angles can be computed for each rotor core, at 460. For example, each node on trajectory (or subtrajectory) has an associated vector formed by the corresponding wave front line. For adjacent nodes in time, the rotation angle for a rotor can be determined by calculating the angle change between these two vectors over time. As another example, a plane along heart surface where the rotor stays can be identified and all the vectors formed by wave front lines can be projected on to this plane. The rotation angles can be computed by creating two orthogonal axes in the plane to calculate the angles of projected vectors. As yet another example, a plane can be identified based on principle components of the nodes along trajectory. Then all vectors associated with nodes/wave front lines can be projected onto this plane, and two orthogonal axes in such plane can be determined and used to calculate angles across time. Other methods to calculate rotation angles for rotors could also be used at 460.

At 462, rotor statistics can be computed for each spatially stable portion of the rotor. Examples of rotor statistics can include rotor rotation cycle length, direction of rotation (e.g., clockwise or counter-clockwise), angular velocity statistics (mean, average, standard deviation of velocity) rotor counts per time interval, rotor acceleration, or other information about rotors and their respective trajectories. At 464 rotors can be filtered based upon applying threshold statistics, which can be set to respective predetermined values or can be programmable in response to a user input. The threshold statistics thus can be utilized filter each of the identified rotors based on their respective statistics (computed at 462) to identify a set of sub trajectories that exhibit characteristics within the constraints defined by the threshold statistics.

At 466, based upon the filtering by the statistics at 464, stable rotors with corresponding trajectories can be determined. At 468, additional statistics can then be computed for each of the stable rotors determined at 466. The rotor statistics computed at 468 can include the same or different statistics that were utilized to filter but instead are applied to the stable portions of the rotor core trajectories that have been determined. The additional statistics can include statistics computed from one or from multiple stable rotors at 466. For example, the statistics computed at 468 can be implemented to determine a regional mean and standard deviation for a corresponding local region or globally, such as an average number of rotations, rotational cycle length and the like.

At 470, one or more stable rotor maps can be generated to depict the one or more statistics associated with one or more stable rotors (e.g., phase, rotation angle, angular velocity, rotor counts, cycle length counts and the like) over time the maps generated can be a static map displaying the relevant information of the maps can be dynamic and vary over time such as according to the time index for which the stable rotor portion is associated. In addition to statistics associated with each stable rotor portion, at 472, statistics can also be determined for a subset of nodes determined to surround the corresponding stable portion, such as demonstrated in the example of FIG. 25. For example, the electrical activity (e.g., electrograms) surrounding a given stable rotor core can be used to demonstrate activation patterns around rotor core. Additional, statistics (e.g., rotor cycle length and the like) thus can be computed at these locations and visualized, such as by generating one or more maps.

In addition to determining information for individual stable rotors, the method 450 can also be utilized to ascertain relative or relationships among stable rotor portions. Such relationships can include connectivity. At 480, rotor connectivity can be determined for each of the rotor core trajectories determined at 454. For example, an identifier for a corresponding wave front line can be tagged a data that is stored in conjunction with each rotor core trajectory for each time index. At 482, connectivity amongst stable rotors determined at 466 can be determined based upon the connectivity information that has been tagged to the trajectory data. For example, the connectivity identifiers for different wave front lines can be compared over a range of time indices between different stable rotor portions that exist concurrently in such time indices to determine if a common wave front line is connected between the trajectories in each of the stable rotor portions. If such connectivity exists for a sufficient period of time, at 484, the stable rotor portions can be identified as a stable pairing of connected rotors. The temporal aspect of the connectivity can be based on the number of time samples or a relative fraction of time samples such as disclosed herein.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more non-transitory computer-readable media having instructions executable by a processor to perform a method of analyzing cardiac electrophysiological signals on a cardiac envelope, the method comprising:
   determining wave break points for each identified cardiac wave front line at a given time sample of a plurality of time samples of the cardiac electrophysiological signals;
   for each other of the plurality of time samples:
      evaluating a spatial distance for a given wave break point relative to each active trajectory in a previous time sample to identify a closest active trajectory;
      appending the given wave break point to update the closest active trajectory based on the evaluating; and
      repeating the evaluating and the appending for each wave break point over the plurality of time samples to generate a set of at least one rotor trajectory;
   computing a stability value for each of the least one rotor trajectory based on at least one of a temporal, angular and spatial characteristic for each respective rotor trajectory;
   identifying at least one stable subtrajectory of each of the least one rotor trajectory based on the stability value relative to a stability threshold value, wherein the stability threshold value is one of a temporal stability threshold value indicative of a minimum subtrajectory lasting time, an angular stability threshold value indicative of a minimum angular characteristic that is determined for a respective rotor subtrajectory based on rotation angles along the respective rotor subtrajectory, or a spatial stability threshold value indicative of a maximum subtrajectory component distance from a centroid of a respective subtrajectory;

generating and displaying on a display a graphical map that includes a visualization of the at least one stable subtrajectory on a graphical representation of the cardiac envelope.

2. The one or more media of claim 1, wherein the angular characteristic comprises at least one of a rotation rate for a rotor corresponding to the least one rotor trajectory, an angular acceleration for the rotor, a number of rotations for the rotor, a rotation cycle length for the rotor, and a direction of rotation for the rotor for a plurality of time samples.

3. The one or more media of claim 1, the method further comprising beginning a new trajectory with the given wave break point if the evaluating indicates that the closest active trajectory for a current time sample is greater than a predetermined distance or if the closest active trajectory already has been updated for the current time sample.

4. The one or more media of claim 1, wherein the at least one stable subtrajectory comprise at least two stable subtrajectories, the method further comprising computing an indication of connectivity between the at least two stable subtrajectories based on a number of at least one wave front line linking the at least two stable subtrajectories.

5. The one or more media of claim 4, wherein the method further comprises determining that at least two of the stable subtrajectories are stably connected based on the indication of connectivity exceeding a time-based threshold.

6. The one or more media of claim 1, wherein the method further comprises computing an index representing a sustainability of at least one arrhythmia driver residing within at least one spatial region on a geometric surface, wherein the index comprises a value to quantify the sustainability of the at least one arrhythmia driver.

7. The one or more media of claim 6, wherein the index is computed based on an average number of rotations by one or more rotors residing within a spatial region on the geometric surface.

8. The one or more media of claim 1, wherein the method further comprises controlling at least one therapy delivery parameter based on stored arrhythmia driver data corresponding to the set of at least one rotor trajectory.

9. The one or more media of claim 1, wherein the wave front lines are generated by:
computing phase values for a plurality of nodes distributed across a geometric surface based on data representing electrical activity for the plurality of nodes over time;
evaluating the computed phase values for each of the nodes at a given time to identify each pair of adjacent nodes having phase values that encompass a predetermined phase threshold; and
determining at least one location on the geometric surface, corresponding to a wave front at the given time, based on the evaluating; and
wherein determining the wave break points for a current time sample is computed for each non-spatially looping wave front line generated for the current time sample.

10. The one or more media of claim 1, the method further comprising displaying the graphical map in substantially real time as electrical signals on which the cardiac electrophysiological signals are based are measured from a body surface.

11. A system for analyzing cardiac electrophysiological signals on a cardiac envelope, the system comprising:
memory to store machine readable instructions and data, the data comprising cardiac electrical data representing cardiac electrical activity for a plurality of nodes distributed across a geometric surface representative of the cardiac envelope over a plurality of time samples of the cardiac electrophysiological signals;
at least one processor to access the memory and execute the instructions, the instructions comprising:
an arrhythmia driver analyzer comprising:
a trajectory detector programmed to compute wave break points for each of a wave front lines computed based on phase information derived from the cardiac electrical data from the plurality of nodes distributed across the geometric surface for each of the plurality of time samples and to determine a rotor trajectory for at least one rotor core across the geometric surface based on applying temporal and/or spatial constraints to the wave break points through a sequence of the plurality of time samples, the determined rotor trajectory being stored as arrhythmia driver data in the memory; and
a stability detector programmed to identify at least one stable rotor portion corresponding to subtrajectories of the determined rotor trajectory based on a stability value relative to a stability threshold value, the stability value being computed based on at least one of a temporal, angular and spatial characteristic of the determined rotor trajectory, the stability threshold value being one of a temporal stability threshold value indicative of a minimum subtrajectory lasting time, an angular stability threshold value indicative of a minimum angular characteristic that is determined for a respective rotor subtrajectory based on rotation angles along the respective rotor subtrajectory, or a spatial stability threshold value indicative of a maximum subtrajectory component distance from a centroid of a respective subtrajectory, each identified stable rotor portion being stored as the arrhythmia driver data in the memory; and
a map generator to generate a graphical map based on the arrhythmia driver data that includes a graphical representation of at least one of the determined rotor trajectory and the identified stable rotor portions with respect to a graphical representation of the surface; and
at least one display to display the graphical map.

12. The system of claim 11, wherein the instructions further comprise a wave front analyzer programmed to compute the wave front lines extending over a surface for each of the plurality of time samples based on the phase information computed from the electrical data at nodes distributed across the geometrical surface for each of the plurality of time samples.

13. The system of claim 12, wherein the trajectory detector is further programmed to:
compare a spatial distance for a given wave break point relative to another wave break point through the sequence of the time samples relative to a predetermined threshold distance; and append the other wave break point to the given wave break point through the sequence of time samples to define the rotor trajectory of the at least one rotor core if the spatial distance is less than the predetermined threshold distance.

14. The system of claim 11, further comprising a therapy system configured to control at least one therapy delivery parameter based on the stored arrhythmia driver data.

15. The system of claim 11, wherein the arrhythmia driver analyzer further comprises a driver sustainability module programmed to compute an index based on determining an average number of rotations by one or more rotors residing within a designated spatial region of a surface, the index representing a sustainability of at least one arrhythmia driver.

16. One or more non-transitory computer-readable media having instructions executable by a processor, the instructions programmed to perform a method of analyzing cardiac electrophysiological signals on a cardiac envelope, the method comprising:
  determining wave break points for each identified cardiac wave front line at a given time sample of a plurality of time samples of the cardiac electrophysiological signals;
  for each other of the plurality of time samples:
    evaluating a spatial distance for a given wave break point relative to each active trajectory in a previous time sample to identify a closest active trajectory, each respective trajectory in the previous time sample being an active trajectory if updated within a predetermined time period from a current time sample time;
    appending the given wave break point to update the closest active trajectory based on the evaluating; and
    repeating the evaluating and the appending for each wave break point over the plurality of time samples to generate a trajectory for at least one rotor;
  computing a stability value for each of the at least one rotor based on an angular characteristic determined for each respective rotor trajectory, wherein the angular characteristic is determined based on rotation angles along the respective rotor trajectory; and
  generating and displaying on a display a graphical map that includes a visualization of the at least one rotor on a graphical representation of the cardiac envelope.

17. The one or more media of claim 16, wherein the method further comprises identifying at least one stable subtrajectory of each respective rotor trajectory based on the stability value relative to a stability threshold value.

18. The one or more media of claim 17, wherein the angular characteristic comprises at least one of a direction of rotation of the at least one rotor, an angular velocity of the at least one rotor, rotation rate of the at least one rotor or angular acceleration of the at least one rotor.

* * * * *